United States Patent
Schramm et al.

(10) Patent No.: US 8,075,910 B2
(45) Date of Patent: Dec. 13, 2011

(54) ORAL COMPOSITIONS COMPRISING EDIBLE OILS AND VITAMINS AND/OR MINERALS AND METHODS FOR MAKING ORAL COMPOSITIONS

(75) Inventors: Jack H. Schramm, Gordonsville, VA (US); James W. McGrath, Jr., Keswick, VA (US)

(73) Assignee: PBM Pharmaceuticals, Inc., Charlottesville, VA (US)

(*) Notice: Subject to any disclaimer, the term of this patent is extended or adjusted under 35 U.S.C. 154(b) by 1284 days.

(21) Appl. No.: 11/040,953

(22) Filed: Jan. 21, 2005

(65) Prior Publication Data
US 2006/0188607 A1    Aug. 24, 2006

Related U.S. Application Data

(60) Provisional application No. 60/584,655, filed on Jun. 30, 2004, provisional application No. 60/572,787, filed on May 20, 2004.

(51) Int. Cl.
*A61K 47/00* (2006.01)
*A61K 9/48* (2006.01)
*A61K 9/20* (2006.01)

(52) U.S. Cl. ......... 424/439; 424/451; 424/464; 424/465

(58) Field of Classification Search .................. None
See application file for complete search history.

(56) References Cited

U.S. PATENT DOCUMENTS

| | | | | |
|---|---|---|---|---|
| 2,348,503 A * | 5/1944 | Taylor | | 514/474 |
| 2,562,840 A * | 7/1951 | Caldwell | | 514/725 |
| 2,720,463 A | 10/1955 | Stirn et al. | | |
| 3,376,199 A | 4/1968 | Leonard et al. | | |
| 3,427,378 A | 2/1969 | Henderson et al. | | |
| 3,553,329 A | 1/1971 | Nelson et al. | | |
| 3,861,941 A | 1/1975 | Brockett | | |
| 4,016,254 A | 4/1977 | Seager | | |
| 4,154,820 A | 5/1979 | Simoons | | |
| 4,260,626 A | 4/1981 | Carr et al. | | |
| 4,454,125 A * | 6/1984 | Demopoulos | | 514/52 |
| 4,534,467 A * | 8/1985 | Rathbun | | 206/530 |
| 4,545,125 A * | 10/1985 | Rogers et al. | | 33/572 |
| 4,623,488 A * | 11/1986 | Takao | | 554/224 |
| 4,631,284 A | 12/1986 | Salpekar et al. | | |
| 4,670,285 A * | 6/1987 | Clandinin et al. | | 426/602 |
| 4,792,418 A | 12/1988 | Rubin et al. | | |
| 4,843,095 A * | 6/1989 | Rubin | | 514/558 |
| 4,913,921 A * | 4/1990 | Schroeder et al. | | 426/321 |
| 4,915,965 A | 4/1990 | Tanaka | | |
| 4,931,284 A | 6/1990 | Ekamn et al. | | |
| 4,987,031 A | 1/1991 | Tatematsu et al. | | |
| 5,275,821 A | 1/1994 | Torosian | | |
| 5,346,709 A * | 9/1994 | Myhre | | 426/111 |
| 5,374,657 A * | 12/1994 | Kyle | | 514/547 |
| 5,407,957 A * | 4/1995 | Kyle et al. | | 514/547 |
| 5,434,183 A * | 7/1995 | Larsson-Backstrom | | 514/549 |
| 5,494,678 A | 2/1996 | Paradissis et al. | | |
| 5,525,355 A | 6/1996 | Brown et al. | | |
| 5,563,129 A * | 10/1996 | Masuya et al. | | 514/120 |
| 5,571,441 A | 11/1996 | Andon et al. | | |
| 5,770,225 A | 6/1998 | Parekh et al. | | |
| 5,869,084 A | 2/1999 | Paradissis et al. | | |
| 5,906,833 A | 5/1999 | Klatz | | |
| 5,916,591 A | 6/1999 | Bierdel-Willkommen et al. | | |
| 5,919,482 A | 7/1999 | Marttila et al. | | |
| 5,925,381 A | 7/1999 | Boyle et al. | | |
| 5,925,669 A * | 7/1999 | Katz et al. | | 514/449 |
| 6,077,531 A | 6/2000 | Salin-Drouin | | |
| 6,096,317 A | 8/2000 | DeSantis et al. | | |
| 6,096,338 A | 8/2000 | Lacey et al. | | |
| 6,190,680 B1 | 2/2001 | Sakurada et al. | | |
| 6,190,694 B1 | 2/2001 | Mizushima et al. | | |
| 6,190,702 B1 | 2/2001 | Takada et al. | | |
| 6,267,985 B1 | 7/2001 | Chen et al. | | |
| 6,280,767 B1 | 8/2001 | Sano | | |

(Continued)

FOREIGN PATENT DOCUMENTS

CN    1225837    8/1999

(Continued)

OTHER PUBLICATIONS

DHA as Brain Food, http://web.archive.org/wb/20010827172018/http:///www.askdrsears.com/html/4/t040900.asp, accessed online on May 17, 2009.*  Dr. Decuypere's Nutrient Chart, Fruit Chart.*
Physician's Desk Reference (49th Edition, 1995), p. 1264.
Basit el al., "The Effect of Polyethylene Glycol 400 on Gastrointestinal Transit . . . " Pharmaceutical Research (USA), vol. 18, 1146-1150 (2001).
Veldkamp et al., "Steady State Pharmacokinetics of Twice Daily dosing . . . " Journal of Acquired Immune Deficiency Syndrome 27(4), 344-349 (2001).
Raquel D. Petry,"The Influence of Adjuvants and Filling Method . . . " Revista Brasileira de Farmacia 79(3/4), 99-103 (1998).
Shehab et al., "Studies on the In Vitro Release of Ibuprofen from . . . " Drug Dev. Ind. Pharm. 22 No. 7, 645-51 (1996).

(Continued)

*Primary Examiner* — Robert A Wax
*Assistant Examiner* — Melissa Mercier
(74) *Attorney, Agent, or Firm* — Locke Lord LLP; David G. Greene; Peter J. Fallon

(57) ABSTRACT

The present invention provides oral dosage compositions, and methods of making thereof, which contain an edible oil, preferably containing an omega-3 fatty acid, and admixed therein one or more water soluble vitamins and/or minerals, for example vitamins B6, B9, and/or B12. The present invention also provides a method of making the composition comprising mixing the edible oil and one or more water-soluble vitamins and/or minerals to form a suspension or emulsion of the water-soluble vitamins and/or minerals in the edible oil. The mixture can be inserted into capsules, gelcaps, or caplets for oral consumption. An additional aspect of the invention is that the edible oil can coat particles of the water-soluble vitamins and/or minerals, which may preferably provide the vitamins and/or minerals improved absorption in the body due to increased resistance to degradation in the acidic environment of the stomach.

44 Claims, No Drawings

U.S. PATENT DOCUMENTS

| | | | |
|---|---|---|---|
| 6,365,181 B1 | 4/2002 | Matthews | |
| 6,376,461 B1 | 4/2002 | Igari et al. | |
| 6,403,119 B2 * | 6/2002 | Oppenheim et al. | 424/458 |
| 6,413,463 B1 | 7/2002 | Yamamoto | |
| 6,433,025 B1 | 8/2002 | Lorenz | |
| 6,485,752 B1 * | 11/2002 | Rein | 424/523 |
| 6,506,406 B1 | 1/2003 | Shioya | |
| RE38,009 E | 2/2003 | Garnett et al. | |
| 6,534,093 B1 | 3/2003 | Thosar | |
| 6,541,025 B1 | 4/2003 | Kershman et al. | |
| 6,544,553 B1 | 4/2003 | Hsia et al. | |
| 6,551,615 B1 | 4/2003 | Iyer | |
| 6,569,445 B2 | 5/2003 | Manning et al. | |
| 6,576,253 B2 | 6/2003 | Manning et al. | |
| 6,808,725 B2 * | 10/2004 | Bailey et al. | 426/72 |
| 6,838,091 B2 | 1/2005 | Lipari et al. | |
| 2002/0035087 A1 | 3/2002 | Barclay | |
| 2002/0192265 A1 | 12/2002 | Manning et al. | |
| 2003/0012797 A1 | 1/2003 | Ishikawa | |
| 2003/0021839 A1 | 1/2003 | Draisey | |
| 2003/0072797 A1 | 4/2003 | Guinez et al. | |
| 2003/0072808 A1 | 4/2003 | Thosar | |
| 2003/0108594 A1 | 6/2003 | Manning et al. | |
| 2004/0044028 A1 * | 3/2004 | Obukowicz | 514/303 |
| 2004/0052922 A1 | 3/2004 | Pistolesi | |
| 2004/0106584 A1 * | 6/2004 | Arterburn et al. | 514/165 |

FOREIGN PATENT DOCUMENTS

| | | |
|---|---|---|
| CN | 1248451 | 3/2000 |
| CN | 1284379 | 2/2001 |
| CN | 1301556 | 7/2001 |
| CN | 1317323 | 10/2001 |
| CN | 1325688 | 12/2001 |
| EP | 1 163 901 | 12/2001 |
| EP | 0 711 152 | 12/2002 |
| FR | 2 627 671 | 9/1989 |
| FR | 2 639 797 | 6/1990 |
| GB | 2 028 655 | 3/1980 |
| JP | 59157018 | 9/1984 |
| JP | 61282054 | 12/1986 |
| JP | 4082827 | 3/1992 |
| JP | 2002188095 | 7/2002 |
| JP | 2003073230 | 12/2003 |
| WO | WO 92/00066 | 1/1992 |
| WO | WO 95/09614 | 4/1995 |
| WO | WO 95/31972 | 11/1995 |
| WO | WO 02/28365 | 4/2002 |
| WO | WO 02/052955 | 7/2002 |
| WO | WO 03/013550 | 2/2003 |
| WO | WO 2005/112654 | 12/2005 |

OTHER PUBLICATIONS

L. Conings et al., "Stability Study of Cimetidine 200mg and Cimetidine . . . " Farmaceutisch Tijdschrift voor Belgie (Belgium), vol. 73, 2-21 (Sep. 1996).

Abdallah et al., "Liquid Chromatographic Determination of Rutin . . . " Journal of Liquid Chromatography 16(18), 4107-4116 (1993).

Dahl et al., "Feasibility of Manufacturing a Solid Dosage Form using . . . " Drug Development and Industrial Pharmacy 16(12), 1881-1891 (1990).

Topaloglu, "A HArd Gelatin Capsule Formulation for Amphotalide," Acta Pharmaceutica Turcica 32(1), 11-16 (1990).

Hannula, "Release of Ibuprofen from Hard Gelatin Capsule Formulation . . . " Effect of Modern Disintegrants, Acta Pharm. Fenn.. 98, No. 3, 189096 (1989).

Kensley et al., "Multidimensional Column-Switching Liquid . . . " J. Pharm. Sci. 75, No. 10, 999-1002 (1986).

Pfeifer et al., "Investigations of the Frequency and Causes of Dosage Errors . . . " Drugs Madde Ger. 29, No. 4, 217-218, 220, (1986).

Serajuddin et al., "Water Migration from Soft Gelatin Capsule . . . " J. Pharm. Sci. 75, No. 1, 62-64 (1986).

Pfeifer et al., "Untersuchugen zur Haufigkeit und Ursachen . . ." Pharm. Ind. 46, 8, 860-63 (1984).

Pfeifer et al., "Untersuchugen zur Haufigkeit und Ursachen . . . " Pharm. Ind. 47, 4, 423-425 (1984).

Mura et al., "In Vitro Study of Some Factors Affecting Diffusion of . . . " Bollettino Chimico Farmaceutico 123 (7), 344-51 (1984).

Byoin et al., "Pharmaceutical Study on Ubidecarenone Soft Gelatin Capsule," Byoin Yakugaku 9(3), 273-7 (1983).

Steinbach et al., "Studies on the Pharmaceutical and Biological availability of diazepam . . . " Pharmazeutische zeitung 125(27), 1297-9 (1980).

James et al., "Availability of Tritium from Nonaqueous Solutions of . . . " Journal of Pharmacy and Pharmacology 32(12), 810-814 (1980).

Newton et al., "The Influence of Additives on the Presentation of a Drug . . . " Journal of Pharmacy and Pharmacology 29(5), 294-7(1977).

Foo S. Hom, "Separation and Ultraviolet Absorbance Techniques for . . . " Journal-Association of Official Analyical Chamists 60(1), 48-51 (1977).

www.allabout-solgar-vitamins.com, May 12, 2003, (2 pages).
wwvv.bioceuticsinternational.com/products/epo090.htm, May 12, 2003 (2 pages).
www.worldwideshopingmall.co, May 12, 2003 (2 pages).
www.vitapure.com, May 12, 2003(1 page).
www.healthaid.co, May 12, 2003 (4 pages).
http://vitaminlady.com/Jarrow/Allcaps.asp, May 12, 2003 (2 pages).
www.health-store.co.uk, May 12, 2003 (2 pages).
wwvv.vitamer.com/vit ad.asp, May 12, 2003 (4 pages).
www.vitaminretailer.com, May 12, 2003 (6 pages).
www.health.egnet.net, May 12, 2003 (4 pages).
www.egyfit.com, May 12, 2003 (4 pages).

International Search Report which was cited in a corresponding PCT counterpart application (PCT/US2005/017413), completed on Jun. 13, 2008 and published on Apr. 2, 2009.

International Preliminary Report on Patentability and a Written Opinion of the International Searching Authority which was cited in a corresponding PCT counterpart application (PCT/US2005/017413), completed on Jun. 13, 2008 and issued on Mar. 3, 2009.

"Efficacy and safety of plant stanols and sterols in the management of blood cholestrol levels" Katan et al. Mayo Clinic Proceedings, 2003, 78 965-978.

Martin B. Katan et al., "Efficacy and Safety of Plant Stanols and Sterols in the Management of Blood Cholesterol Levels," Mayo Clin. Proc., Aug. 2003, vol. 78, pp. 965-978.

Akhlaq A. Farooqui, "Beneficial Effects of Fish Oil on Human Brain," Department of Molecular and Cellular Biochemistry, Springer Science + Business Media, LLC 2009.

WorldHealth.net, "Omega-3 Fatty Acid, Fish Oil, DHA (docosahexaenoic acid), EPA (eicosapentaenoic acid)," Posted on 2005 in Fatty Acids, Lipids & Oils.

* cited by examiner

ORAL COMPOSITIONS COMPRISING EDIBLE OILS AND VITAMINS AND/OR MINERALS AND METHODS FOR MAKING ORAL COMPOSITIONS

PRIOR PATENT APPLICATIONS

This application claims priority to prior Provisional patent application U.S. Ser. No. 60/584,655 filed Jun. 30, 2004, and prior Provisional patent application U.S. Ser. No. 60/572,787 filed May 20, 2004. The contents of each of these two patent applications are incorporated in this application in their entirety by reference.

BACKGROUND OF THE INVENTION

Field of the Invention

The present invention is directed to methods and compositions that combine nutritional, health and/or medical benefits provided to mammals by edible oils, particularly by omega-3 fatty acids, with nutritional, health and/or medical benefits provided to mammals by vitamins and minerals, particularly by B vitamins.

The present invention relate to compositions for an oral administration to mammals comprising one or more edible oils and one or more water soluble vitamins and/or minerals. The one or more edible oils preferably include one or more omega-3 fatty acids, and are uniformly combined. The one or more vitamins and/or minerals preferably include one or more water-soluble and oil-insoluble B vitamins, and more preferably include vitamin B6 (pyridoxine), vitamin B9 (folic acid or folate) and/or vitamin B12 (cyanocobalamin, cobalamin, cobalamin bound to recombinant intrinsic factor (rhIF) and/or reduced forms of cobalamin), which may be present in any combination. The one or more vitamins and/or minerals preferably are present in a solid state, and in the form of a uniform mixture, and are uniformly suspended within the one or more edible oils, or are present within an emulsion (wherein such oil phase includes the one or more edible oils).

The present invention also relates to methods for producing such compositions, and to methods for using such compositions to provide one or more nutritional, health and/or medical benefits to a mammal, or to enhance one or more of such benefits in a mammal.

Examples of water-soluble vitamins include the B-vitamins, and more particularly, at least one of vitamin B6, vitamin B9, and vitamin B12, or any combination thereof. The water-soluble vitamins and/or minerals are optionally present in a solid-state form, such as an amorphous powder or a milled material, for example, a finely milled crystalline material, but can also be present in solution as part of an emulsion of an aqueous solution and the edible oils.

Water-soluble vitamins and/or minerals present in solid form in compositions of the invention preferably become at least temporarily suspended in, and coated with, one or more edible oils. For example, in one embodiment of the invention, a solid form including a uniform mixture of the water-soluble B vitamins B6, B9 and B12 is coated with, and suspended within, an omega-3 oil. While not wishing to be bound by theory it is presently believed that, as a result of the vitamins and/or minerals being coated by an edible oil, compositions within the present invention may have an enhanced ability to transport water-soluble vitamins and/or minerals through the stomach of a mammal, which generally is a highly acid environment that is maintained by the secretion of hydrochloric acid, without being degraded and, thus, permitting some or all of the water-soluble vitamins and/or minerals to be delivered to the intestinal tract, where they can be absorbed and delivered to other parts of the mammal's body, such as the capillaries, the lymphatic system and the circulatory system, and produce a beneficial effect.

Compositions within the invention may be employed to provide, or enhance, nutritional, medical and/or other health benefits to mammals, whether in satisfactory health or suffering from one or more conditions, illnesses, diseases or disorders, including depression, dementia, Alzheimer, schizophrenia, rheumatoid arthritis, non-specific arthritis, osteoarthritis, osteoporosis, diabetes, neurological development and degeneration, allergic and immunologic disorders, cancer, pregnancy, lactating women, and disease states effected or characterized by elevated blood pressure, low HDL, arrhythmia, elevated levels of homocysteine, triglycerides and c-reactive protein and low levels of the components of the invention.

Nutritional and Medical Benefits Provided by Edible Oils and Fatty Acids

Edible fats and oils generally provide nutritional and health benefits to mammals. Fats are one of the three main classes of food, and are the most concentrated form of metabolic energy available to humans. Fats and oils are sources of essential fatty acids, an important dietary requirement, as well as other nutritious fatty acids.

Clinical studies have shown that certain edible oils containing DHA (an "omega-3" fatty acid) and other fatty acids can provide significant medical benefits to mammals, particularly to human beings. For example, both omega-3 and omega-6 fatty acids are associated with a lower risk of coronary heart disease. [Frank B. Hu, M. D. et al., "Types of Dietary Fat and Risk of Coronary Heart Disease: A Critical Review," J Am Coll Nutr. 20(1): 5-19 (2001).]

Other publications that discuss the nutritional, health and/or medical benefits provided by edible oils include Elda Hauschildt, "Alpha-Linolenic Acid may help Prevent Heart Disease," Am J Clin Nutr. Vol. 75, 221-227 (2002); Yvonne E. Finnegan et al., "Plant- and Marine-Derived n-3 Polyunsaturated Fatty Acids have Differential Effects on Fasting and Postprandial Blood Lipid Concentrations and on the Susceptibility of LDL to Oxidative Modification in Moderately Hyperlipidemic Subjects," Am J Clin Nutr., Vol. 77, 783-795 (2003); Rozenn N. Lemaitre et al., "n-3 Polyunsaturated Fatty Acids, Fatal Ischemic Heart Disease, and Nonfatal Myocardial Infarction in Older Adults: the Cardiovascular Health Study," Am J Clin Nutr., Vol. 77, 319-325 (2003); Dayong Wu et al., "Effect of Dietary Supplementation with Black Currant Seed Oil on the Immune Response of Healthy Elderly Subjects," Am J Clin Nutr. Vol. 70(4), 536-543 (1999); Frank B. Hu et al., "Dietary Intake of α-Linolenic Acid and Risk of Fatal Ischemic Heart Disease Among Women," Am J Clin Nutr. Vol. 69, 890-897 (1999); and E H Temme et al., "Comparison of the Effects of Diets Enriched in Lauric, Palmitic, or Oleic Acids on Serum Lipids and Lipoproteins in Healthy Women and Men," Am J Clin Nutr., Vol 63, 897-903 (1996).

Fatty acids, such as "omega-3" fatty acids (also known as "n-3" fatty acids), "omega-6" fatty acids, "omega-9" fatty acids and essential fatty acids are generally present in high levels in various edible oils. "Omega-3 fatty acids" are the n-3 family of polyunsaturated fatty acids, and are called "n-3 fatty acids" because the first double bond occurs in the third carbon bond counting from the end or omega position of the fatty acid. Omega-3 fatty acids have many nutrition, health and/or medical benefits associated with them, and thus, can provide numerous beneficial effects to human beings and a wide variety of animals that ingest them, whether the consumers are healthy or have one or more diseases or disorders.

Although omega-3 fatty acids can be obtained from other sources, such as plant oils, fish have a unique ability to provide high levels of various specific fatty acids, such as omega-3 fatty acids docosahexaenoic acid (DHA) and eicosapentaenoic acid (EPA). Omega-3 fatty acids include, for example, docosahexaenoic acid (DHA), docosapentaenoic acid, alpha-linolenic acid (ALA), eicosapentaenoic acid (EPA), eicosatetraenoic acid, moroctic acid and heneicosapentenoic acid. Omega-3 fatty acids are precursors of eicosanoids (prostaglandins, thromboxanes and leukotrienes), which are signal substances (cell messengers) that have a widely different effect upon biological activity. Many of these signal substances regulate physiological and immunological reactions.

Omega-3 fatty acids have been shown to be beneficial in the prevention of cardiovascular pathology, the reversal of atherosclerosis, the inhibition of tumor formation and the development and the regulation of serum cholesterol. Prospective cohort studies and secondary prevention trials have provided strong evidence that an increasing intake of n-fatty acids from fish or plant sources substantially lowers risk of cardiovascular mortality. [Frank B. Hu, M. D. et al., "Types of Dietary Fat and Risk of Coronary Heart Disease: A Critical Review," supra.] Other research suggests the therapeutic value of oils rich in omega-3 unsaturated fatty acids for disorders related to blood hyperviscosity, including the lowering of serum cholesterol and the suppression or reduction of plasma triglycerides, inflammatory autoimmune disorders, tumors and various other disorders. [D. F. Horrobin, "Clinical uses of Essential Fatty Acids," Eden. Press, London, 1982.] The omega-3 fatty acids also suppress the production of the proinflammatory cytokines tumor necrosis factor (TNF), particularly TNF alpha, interleukin-1 (IL-1) and thromboxanes. The protective effects of n-3 fatty acids are likely a result of multiple mechanisms, including reducing triglyceride levels, reducing platelet aggregation and antiarrhythmic effects.

Omega-3 fatty acids are also essential for the normal development of an unborn baby's brain, especially during the third trimester, when the size of a baby's brain increases threefold. If a baby's mother fails to have a sufficient quantity of omega-3 fatty acids in her diet, the fetus will generally depend upon the mother's brain tissue and tissue storage of these omega-3 fatty acids. Lab tests have shown that new mothers have approximately one half of the normal blood levels of omega-3 fatty acids.

Linolenic acid, a polyunsaturated fatty acid having three double bonds, is a precursor to EPA and DHA, and is considered to be a dietary essential fatty acid. Because the body is not capable of synthesizing linolenic acid, it must be acquired from a dietary source, such as food or supplements.

DHA is an omega-3 long-chain fatty acid that is the primary structural fatty acid in the gray matter of the brain, and in the retina of the eye, and accumulates during the fetal period and during the first year after birth. DHA is essential for normal visual and neurological (nervous system) development in infants, and for normal brain and eye function in adults. It is necessary for brain and eye development, growth and learning ability in children. [A. P. Simopoulos, "Omega-3 Fatty Acids in Health and Disease and in Growth and Development," American Journal of Clinical Nutrition 54, No. 3, 438-463 (1991).]

The human body only synthesizes small quantities of DHA. As a result, it is necessary to obtain DHA from dietary sources. The primary source of DHA is fatty fish, such as mackerel, salmon, herring, sardines, black cod, anchovies and albacore tuna, and oils from the tissues of such fish.

DHA and EPA, which is associated with vascular regeneration, can alter eicosanoid and cytokine production, providing an improved immunocompetence (strengthening immune system activity) and a reduced inflammatory response to injury. The contribution of DHA and EPA to reducing the incidence of numerous inflammatory/circulatory disorders, cardiac problems, premature births, cognitive ability in children and mental well being has been well documented.

ALA is an essential omega-3 fatty acid for humans. Adequate intake of ALA and long-chain omega-3 fatty acids is especially important for infants, young children and patients requiring parenteral and enteral nutrition. Experimental studies have suggested an antiarrhythmic effect of ALA, and beneficial effects of ALA on cardiovascular disease. [Frank B. Hu, M. D. et al., "Types of Dietary Fat and Risk of Coronary Heart Disease: A Critical Review," supra.]

"Omega-6" fatty acids include gamma-linolenic acid (GLA), which is present in Black Current Seed Oil, linoleic acid, which is present in many vegetable oils, and arachidonic acid, which is present in many animal fats and in algae oil. GLA is an n 18:3 omega-6 polyunsaturated fatty acid that has been used in the amelioration of various diseases, such as eczema, rheumatoid arthritis and premenstrual syndrome, and that has been shown to improve the effectiveness of cancer chemotherapy. Arachidonic acid (ARA or AA) is an omega-6 polyunsaturated fatty acid that has been shown to play a role in early neurological and visual development and is a precursor in the biosynthesis of some prostaglandins.

"Omega-9" fatty acids include, for example, oleic acid, which is present in sunflower oil, olive oil, avocados, canola oil and in many animal fats.

Marine oils (including "fish oils") are oils that are obtained from aquatic lifeforms, either directly or indirectly, particularly from oily fish. Marine oils include, for example, herring oil, cod oil, anchovy oil, tuna oil, sardine oil, menhaden oil and algae oil. Fish that are employed to produce marine oils include, for example, farm-raised or wild, fresh-water or salt-water, fish and shellfish, such as herring, salmon, salmonoids, gadoids, shrimp, cod, carp, tilapia, perch, trout, sturgeon, krill, tuna, flat fish, anchovies, sardines, menhaden, shrimp, Mackerel, eels and seals. Marine oils may also be obtained from marine organisms, such as calanus (Calanus finmarchicus), a 3-4 mm copepod, algae and microalgae, for example, diatoms and dinoflagellates. Peru is currently the world's largest producer of fish oil.

Although omega-3 fatty acids can be obtained from other sources, such as plant oils, fish have a unique ability to provide high levels of the omega-3 fatty acids DHA and EPA. Fish and fish oil are also sources of the "omega-3" fatty acids docosapentaenoic acid, eicosatetraenoic acid, moroctic acid and heneicosapentenoic acid. Marine oils having a total "omega-3" fatty acid content of greater than about 20 weight percent include those derived from menhaden oil, herring, capelin, anchovy, cod liver, salmon oil, sardine oil and mixtures thereof. Oils containing omega-3 fatty acids, such as marine oils and DHA, are also referred to as "omega-3" oils or "n-3" oils.

A low rate of cardiovascular disease in populations that have a high intake of fish, such as Alaskan Native Americans, Greenland Eskimos and Japanese living in fishing villages, suggests that fish oil may be protective against artherosclerosis. [Frank B. Hu, M. D. et al., "Types of Dietary Fat and Risk of Coronary Heart Disease: A Critical Review," supra.] Additionally, research into the blood chemistry of Eskimos, who consume large quantities of fish, showed low levels of low-density lipoproteins (LDL cholesterol) and high levels of high-density cholesterol (HDL cholesterol) in the blood despite a rich diet of fatty fish and seals. [Dyerberg et al., "Fatty Acid Composition of Plasma Lipids in Greenland Eskimos," American Journal of Clinical Nutrition 28, 958-966 (1975).]

It is known that oral administration of fish oil, which contains omega-3 fatty acids, has beneficial effects on cardiovascular function, brain function and has other health benefits. One article reports "a significant, graded, independent inverse association between base-line fish consumption and the 30-year risk of fatal myocardial infarction, particularly non-sudden death from myocardial infarction [that] accounted for the [observation of] lower rates of death from all coronary causes, all cardiovascular causes, and all causes in-association with higher fish consumption . . . " [Daviglus, M. L., et al., N Engl J Med 1997; 336(15):1046-53.]

Another study found that "dietary intake of omega-3 fatty acids, approximately 1.5 g/l for 2 years, modestly mitigated the course of human coronary atherosclerosis, as assessed by angiography. Fewer cardiovascular events were noted." [von Schacky, C., et al, Ann Intern Med. 1999; 130:554-62.] Yet another study found that omega-3 fatty acids found in fish oil reduced the risk of sudden death in men without evidence of prior cardiovascular disease. [Albert, C. M., et al., N Engl J Med 2002; 346(15):1113-18.]

There is growing evidence to suggest that fish oil may improve endothelial dysfunction, an early marker of atherosclerosis. In vitro studies have consistently shown that n-3 fatty acids decrease expression of adhesion molecules on the endothelium, and also decrease leukocyte/endothelium interations. Further, clinical experimental studies have shown that n-3 fatty acid supplementation improves endothelial-dependent vasomotor function. [Frank B. Hu, M. D. et al., "Types of Dietary Fat and Risk of Coronary Heart Disease: A Critical Review," supra.]

Various modified or unmodified fungi, such as filamentous fungi, also have an ability to produce lipids having high levels of vitamins, such as GLA. Modified fungi have been employed to ferment DHA oil. Fungi can be isolated from soil and subsequently fermented using known techniques and conventional shake flasks or fermentation systems.

Many plant oils (including vegetable oils and plant seed oils), such as Evening Primrose oil, Black Currant seed oil, Borage oil, Borage seed oil, safflower oil, sunflower oil, peanut oil, olive oil, corn oil, soybean oil, coconut oil, palm oil, palm kernel oil, rapeseed oil, flaxseed (linseed) oil and cotton seed oil, contain high levels of fatty acids, such as GLA, as well as other fatty acids. For example, flaxseed oil, rapeseed oil and soybean oil contain a large quantity of ALA (about 20% in flaxseed oil and about 7% in unhydrogenated soybean oil). GLA is present in Evening Primrose oil, Black Currant seed oil and Borage seed oil, with the highest level of GLA being present in Borage seed oil. Safflower oil and sunflower oil are rich in linoleic acid. Olive oil contains a significant amount of oleic acid.

Numerous metabolic studies have shown strong cholesterol-lowering effects for vegetable oils that are rich in linoleic oil when substituted for dietary saturated fat. In addition, animal studies have suggested an anti-arrhythmic effect when sunflower oil (rich in linoleic acid) was consumed. [Frank B. Hu, M. D. et al., "Types of Dietary Fat and Risk of Coronary Heart Disease: A Critical Review," supra.]

Plant oils can be extracted from plants or seeds using techniques that are known by those of skill in the art. For example, the highest quality Borage seed oil is generally extracted without hexane or the use of other chemical solvents. Rather, the Borage seed oil is "cold processed" using an expeller-press method of extraction, which simply squeezes the oil out from the seed without the use of heat.

With respect to neurological function, Morris, M. C., et al., Arch Neurol 2003: 60: 940-6, have shown that the omega-3 polyunsaturated fatty acids have "profound effects on membrane functions, leading to change in nerve conduction, neurotransmitter release, neurotransmitter reuptake, and postsynaptic transmitter effects. A large number of animal studies have demonstrated that dietary n-3 fatty acids increased learning acquisition and memory performance . . . " See also, Horrocks, L. A. and Young, K. Y., Pharmacological Research 1999; 40(3):211-25 ("Low levels of DHA are also associated with senile dementia (Alzheimer disease) and schizophrenia." "Chronic alcohol intoxication depletes DHA from membranes of the neurons, leading to the common secondary depression in alcoholism.").

Zanarini, M. C. and Frankenburg, F. R, Am J Psychiatry 2003; 160: 167-9, reports results from a double-blind, placebo-controlled study that are "consistent with the findings of recent reports concerning omega-3-fatty acids as an effective adjunctive treatment for bipolar disorder and recurrent depression."

Thus, there is substantial evidence that omega-3 fatty acids can beneficially affect a variety of diseases. See e.g., Conner, W. E., Am J Clin Nutr 2000; 71(suppl):171S-5S (omega-3 fatty acids "favorably affect atherosclerosis, coronary heart disease, inflammatory disease, and perhaps even behavioral disorders.").

Nutritional and Medicinal Benefits Provided by B-Vitamins and Other Water-Soluble Vitamins and Minerals High levels of homocysteine have been reported to be associated with cardiovascular diseases. Refsum, H. and Ueland, P. M., Annu Rev Medicine 1998; 49:31-62 report that [a]n elevated level of total homocysteine (tHcy) in blood, denoted hyperhomocysteinemia, is emerging as a prevalent and strong risk factor for atherosclerotic vascular disease in the coronary, cerebral, and peripheral vessels, and for arterial and venous thromboembolism." Similarly, Schnyder, G., et al. N Engl J Med 2001: 345(22):1593-1600, report that the level of plasma homocysteine can be reduced significantly with a daily dose of folic acid in an amount of at least 500 micrograms, in combination with vitamin B6 (pyridoxine) and vitamin B12 (cyanocobalamin, cobalamin, and/or reduced forms of cobalamin). "Roughly one half of US adults on a given day consume less than the newly lowered recommended dietary allowance for folate, and an estimated 88% consume less than the levels needed to produce low, stable homocysteine levels." Morrison, H. I., et al. Serum Folate and Risk of Fatal Coronary Heart Disease JAMA 1996; 275(24): 1893-6.

Vitamin B9 (folic acid/folate) is thought to be crucial for proper brain function and plays an important role in mental and emotional health. It aids in the production of DNA and RNA, the body's genetic material, and is especially important during periods of high growth, such as infancy, adolescence and pregnancy. Folic acid also works closely together with vitamin B12 to regulate the formation of red blood cells and to help iron function properly in the body.

Vitamin B9 works closely with vitamins B6 and B12 as well as with the nutrients betaine and S-adenosylmethionine (SAM) to control blood levels of the amino acid homocysteine. Elevated levels of this substance appear to be linked to certain chronic conditions such as heart disease and, possibly, depression and Alzheimer's disease. Some researchers have even speculated that there is a connection between high levels of this amino acid and cervical cancer, but the results of studies regarding this have been inconclusive.

Vitamin B12 (cyanocobalamin, cobalamin, cobalamin bound to recombinant intrinsic factor (rhIF) and/or reduced forms of cobalamin) functions as a methyl donor and works with folic acid in the synthesis of DNA and red blood cells and is vitally important in maintaining the health of the insulation sheath (myelin sheath) that surrounds nerve cells. The classical vitamin B12 deficiency disease is pernicious anemia, a serious disease characterized by large, immature red blood cells. It is now clear though, that a vitamin B12 deficiency can have serious consequences long before anemia is evident. Many elderly people are also deficient because their production of the intrinsic factor needed to absorb the vitamin from the small intestine decline rapidly with age.

Vitamin B12 plays an important role in maintaining a low blood concentration of homocysteine by participating in reactions that recycle homocysteine into methionine. In cases of a deficiency of vitamin B12 the conversion of homocysteine to methionine is inhibited. The resulting raised level of homocysteine has been estimated to be a greater risk factor and predicator for cardiovascular diseases than an increased level of cholesterol, high blood pressure, cigarette smoking, and elevated lipoproteins and hypertension. A B12 deficiency has also been suggested to be an independent risk factor for neural tube birth defects. Neural tube defects (NTDs) are a failure of closure of the neural tube, which includes the spinal cord and the brain, and is among the most devastating of all birth defects. A deficiency of vitamin B12 is thought to result in a lack of methionine, which is the sole precursor to the "universal methylator" (S-adenosylmethionine). S-adenosylmethionine participates in almost all methylation processes in the human body. A lack of S-adenosylmethionine slows the growth and/or closure of the neural tube and thereby increase the risk of NTDs. Lower plasma levels of vitamin B12 has also been associated with breast cancer. Vitamin B12, along with folate and vitamin B6, functions as a coenzyme in the building of components for DNA synthesis. Inadequate levels of vitamin B12 may cause misincorporation of uracil, normally found in RNA, into DNA, which may result in chromosome breaks and disruption of DNA repair. Additionally a deficiency of vitamin B12 may cause aberrant DNA methylation, which has been observed in human tumors. Vitamin B12 deficiency is particularly associated with cognitive impairment and widespread pathology in the central nervous system in the elderly. In cells vitamin B12 is converted to coenzymes, which influence brain function through the one carbon metabolism/methylation cycle. Vitamin B12 is required for the synthesis of methionine and S-adenosylmethionine, which the brain relies on to metabolize homocysteine. Furthermore, S-adenosylmethionine dependant reactions include the formation of neurotransmitters, phospholipids and myelin. Thus, vitamin B12 deficiency may cause nervous system dysfunction in the elderly. A severe and progressive consequence of a deficiency of vitamin B12 is the degeneration of the spinal cord. Classical symptoms include symmetrical parasthesias in the hands and feet leading to numbness, muscle weakness and paralysis.

Need for a Dosage Form Incorporating Both Fatty Acids and B-Vitamins

In view of the significant nutritional, medical and/or other health benefits provided by many edible oils, such as the omega-3 fatty acids DHA, EPA and ALA, and by water-soluble vitamins and/or minerals, such as B-vitamins, it would be beneficial to provide dosage forms for oral administration that include one or more edible oils and one or more B-vitamins that properly disintegrate, thereby allowing the edible oils and B-vitamins to become bioavailable, that may permit the edible oils and B-vitamins to be absorbed by the body without being substantially degraded in the acidic environment of the stomach, and that may have a long shelf life under room temperature conditions. In view of these benefits, compositions within the present invention may be effective for improving cardiovascular function, lowering the incidence of myocardial infarction, improving cardiac arrhythmia problems and/or lowering elevated homocysteine levels which, in turn, may have the benefit of lowering the incidence of heart disease and/or depression.

DESCRIPTION OF THE RELATED ART

The Physicians' Desk Reference (49$^{th}$ Edition, 1995, and 54$^{th}$ Edition, 2000) describes a prenatal vitamin and mineral tablet marketed by Lederle Laboratories (Wayne, N.J.) under the trademark name Materna® (pages 1264 and 1534, respectively).

U.S. Pat. No. 5,494,678 discloses multi-vitamin and mineral supplements for incorporation into tablets, powders, granules, beads, lozenges, capsules and liquids, and administration to a pregnant woman during her first, second and third trimesters of pregnancy. The supplements contain specific regimens of a calcium compound, vitamin D, folic acid, vitamin B12, vitamin B6, and vitamin B1.

U.S. Pat. No. 5,571,441 discloses nutritional supplement compositions containing vitamins, minerals, central nervous system bracers, such as caffeine, and flavenols, that are coadministered in the form of a tablet or capsule, as a powder, or as a liquid form.

U.S. Pat. No. 5,869,084 discloses multi-vitamin and mineral supplements for administration to lactating, non-lactating (but not pregnant) and menopausal women in the form of tablets, powders, granules, beads, lozenges, capsules or liquids.

U.S. Pat. No. 5,906,833 discloses nutritional supplements that contain vitamins.

SUMMARY OF THE INVENTION

The present invention provides compositions for an oral administration to a mammal that include one or more edible oils and one or more other water-soluble vitamins and/or minerals, and that generally properly disintegrate, thereby allowing the edible oils and/or water-soluble vitamins and/or minerals to become bioavailable, permitting the water-soluble vitamins and/or minerals to be absorbed by the body without being substantially degraded in the acidic environment of the stomach, and have a long shelf life under room temperature conditions.

In one aspect, the present invention provides compositions for an oral administration to a mammal comprising:
 (a) one or more water-soluble vitamins and minerals in a combined amount that is effective for providing or enhancing a nutritional, medical or other health benefit to a mammal, wherein the one or more water-soluble vitamins and/or minerals are in a form that is capable of being mixed with one or more edible oils;
 (b) one or more edible oils in a combined amount that is effective for permitting the one or more water-soluble vitamins and/or minerals to be mixed with the one or more edible oils; and
 (c) one or more anhydrous diluents for the powder phase
 (d) optionally, one or more antioxidant agents in a combined amount that is effective for preventing or reducing an oxidation, degradation or other decomposition of the one or more water-soluble vitamins, and/or minerals, or the one or more edible oils;

After compositions within the invention are consumed by a mammal, at least some of the water-soluble vitamins and/or minerals present therein generally have an enhanced ability to travel through an acidic environment of a stomach of the mammal without being partially or fully degraded and into an intestinal tract of the mammal, and to be absorbed into the mammal's body, in comparison with other compositions for oral administration that contain the same water-soluble vitamins and/or minerals; or wherein the compositions have an enhanced stability and/or shelf life in comparison with other compositions for oral administration that contain the same water-soluble vitamins and/or minerals.

In another aspect, the present invention provides compositions for an oral administration to a mammal comprising:

(a) one or more solid-state particles of one or more water soluble vitamins or minerals in a combined amount that is effective for providing or enhancing a nutritional, medical or other health benefit to the mammal;

(b) one or more edible oils that include one or more fatty acids, wherein the one or more fatty acids are omega-3 fatty acids, omega-6 fatty acids or omega-9 fatty acids, and wherein the one or more fatty acids are in a combined amount that is effective for permitting the solid state particles to be at least temporarily suspended therein;

wherein the solid state particles are admixed with the one or more edible oils or at least temporarily suspended therein.

In another aspect, the present invention provides compositions for an oral administration to a mammal comprising:

(a) one or more solid-state particles of one or more water soluble vitamins, wherein the one or more water soluble vitamins are vitamin B6, vitamin B9 or vitamin B12, or a combination thereof, and wherein the one or more water soluble vitamins are in a combined amount that is effective for providing or enhancing a nutritional, medical or other health benefit to the mammal;

(b) one or more edible oils including one or more omega-3 fatty acids in a combined amount that is effective for providing or enhancing a nutritional, medical or other health benefit to the mammal.

wherein the solid-state particles are mixed with the one or more edible oils or at least temporarily suspended therein.

In another aspect, the present invention provides compositions for an oral administration to a mammal comprising:

(a) one or more water soluble vitamins or minerals, or combination thereof, in a combined amount that is effective for providing or enhancing a nutritional, medical or other health benefit to the mammal, wherein the one or more water soluble vitamins or minerals are combined with an amount of water that is sufficient to form an aqueous solution;

(b) one or more edible emulsifiers in a combined amount that is effective to cause or enhance the formation of an emulsion;

(c) one or more edible oils in a combined amount that is effective for forming an oil phase of an emulsion;

wherein the aqueous solution is combined with the one or more emulsifiers and the one or more edible oils in a manner that forms an emulsion.

In another aspect, the present invention provides a method for preparing compositions for an oral administration to a mammal comprising the following steps (in any convenient or possible order):

(a) providing one or more water-soluble vitamins and/or minerals in a combined amount that is effective for providing or enhancing a nutritional, medical or other health benefit to a mammal, wherein the one or more water-soluble vitamins and/or minerals are, optionally, in a solid-state form and/or capable of being suspended within one or more edible oils;

(b) providing one or more edible oils in a combined amount that is effective for permitting the one or more water-soluble vitamins and/or minerals to be at least temporarily suspended therein;

(c) optionally, mixing the one or more water-soluble vitamins and/or minerals for a period of time and under conditions that are sufficient to produce a uniform mixture of the one or more water-soluble vitamins and/or minerals;

(d) optionally, mixing the one or more edible oils for a period of time and under conditions that are sufficient to produce a uniform mixture of the one or more edible oils; and (e) suspending an amount of the one or more water-soluble vitamins and/or minerals, or mixture thereof, within an amount of the one or more edible oils, or mixture thereof, that is effective for producing a suspension of the one or more water-soluble vitamins and/or minerals, or mixtures thereof, within the one or more edible oils, or mixtures thereof.

After the compositions are consumed by a mammal, at least some of the water-soluble vitamins and/or minerals present therein generally have an enhanced ability to travel through an acidic environment of a stomach of the mammal without being partially or fully degraded and into an intestinal tract of the mammal, and to be absorbed into the mammal's body, in comparison with other compositions for oral administration that contain the same water-soluble vitamins and/or minerals; or wherein the compositions have an enhanced stability and/or shelf life in comparison with other compositions for oral administration that contain the same water-soluble vitamins and/or minerals.

In another aspect, the present invention provides a method for preparing compositions for an oral administration to a mammal comprising:

(a) providing one or more solid state particles of one or more water soluble vitamins or minerals, or combination thereof;

(b) providing one or more edible oils including one or more fatty acids in a combined amount that is effective for permitting the one or more water soluble vitamins or minerals to be at least temporarily suspended therein;

(c) optionally, mixing the one or more water soluble vitamins or minerals, or combination thereof, for a period of time and under conditions that are sufficient to produce a uniform mixture of the one or more water soluble vitamins or minerals, or combination thereof;

(d) optionally, mixing the one or more edible oils for a period of time and under conditions that are sufficient to produce a uniform mixture of the one or more edible oils;

(e) suspending, at least temporarily, an amount of the one or more water soluble vitamins or minerals, or combination thereof, within an amount of the one or more edible oils, or combination thereof, that is effective for producing a suspension of the solid-state particles of the one or more water soluble vitamins or minerals, or combination thereof, within the one or more edible oils, or mixtures thereof;

(f) injecting a resulting suspension into an oral dosage form, wherein the oral dosage form is hard or soft capsule, gelatin capsule, caplet or gelatin caplet.

In another aspect, the present invention provides a method for preparing compositions for an oral administration to a mammal comprising:

(a) providing one or more solid-state particles of one or more water soluble vitamins or minerals or combination thereof;

(b) mixing the solid-state particles in an amount of water that is sufficient to form an aqueous solution;

(c) providing one or more edible emulsifiers or a combination thereof;

(d) providing one or more edible oils or combination thereof, including one or more fatty acids;

(e) optionally, mixing the one or more edible oils or combination thereof for a period of time and under conditions that are sufficient to produce a uniform mixture of the one or more edible oils;

(f) mixing the aqueous solution with the one or more edible emulsifiers or combination thereof and the one or more edible oils or combination thereof under conditions that are sufficient to form an emulsion;

(g) injecting the emulsion into a hollow oral dosage form that is a soft or hard capsule, gelatin capsule, caplet or gelatin caplet.

In yet another aspect, the present invention provides a method for enhancing the quantity of one or more water-soluble vitamins and/or minerals that are absorbed by an intestinal tract of a mammal and delivered to the mammal's body after the mammal consumes one or more water-soluble vitamins and/or minerals and/or edible oils comprising administering to the mammal a composition according to claim 1.

In still another aspect, the present invention provides a method for enhancing the nutrition, health and/or medical condition of a mammal comprising administering to the mammal an effective amount of a composition according to claim 1.

In still another aspect, the present invention provides a method for enhancing the nutrition, health and/or medical condition of a mammal comprising administering to the mammal an effective amount of a composition according to claim 18.

The water-soluble vitamins and/or minerals, that may be present in the compositions of the invention may be present alone or in any desired combination of two or more water-soluble vitamins and/or minerals. For example, the compositions may include the vitamins B6, B9 and B12, or other B vitamins, alone or in any desired combination, and in any desired quantity. The water-soluble vitamins and/or minerals employed in the compositions of the invention are, optionally, in solid-state forms and subsequently suspended in one or more edible oils to produce a suspension in which the solid-state vitamins and/or minerals are coated with the one or more edible oils. The water-soluble vitamins and/or minerals can also be present in the compositions in the form of an aqueous solution in combination with an emulsifier that forms an emulsion with the one or more edible oils. The compositions of the present invention are suitable for an oral administration to a mammal, and are typically provided as gelatin capsules, such as soft-gel or hard-gel capsules, but may be provided in any other suitable oral dosage form as is known by those of skill in the art.

Edible oil suspensions of solid-state B and/or other vitamins and/or minerals can be prepared by mixing powdered (e.g., micronized or milled) vitamins and/or minerals so as to form a substantially uniform mixture and subsequently suspending such mixture in one or more edible oils, or mixture thereof, to produce a suspension that is preferably homogeneous, and is capable of remaining as a homogenous suspension at least during the filling step of processes for preparing gel capsules (or other oral dosage forms) with the suspension so as to maximize content uniformity in the various filled gel capsules (or other oral dosage forms).

The stability of water-soluble vitamins and/or minerals present in compositions within the present invention may generally be enhanced in comparison with other oral dosage forms containing the same or similar water-soluble vitamins and/or minerals, for example, those that are prepared in a different manner (i.e. those that do not have one or more solid-state water-soluble vitamins and/or minerals suspended within one or more edible oils). Such an improved stability generally results in the compositions of the invention having an enhanced stability and/or a longer shelf life than would otherwise be achievable, and is likely a result of the solid-state water-soluble vitamins and/or minerals becoming coated with the one or more edible oils and, thus, protected from degradation. Further, for the same reasons, compositions within the present invention generally result in an enhanced absorption of the B vitamins, or other water-soluble vitamins and/or minerals, by the body of the mammal. The oil coated vitamins and/or minerals may generally be delivered into the intestinal tract before being substantially solubilized, which generally prevents or limits the acidic environment of the mammal's stomach from fully degrading, or otherwise substantially diminishing the effectiveness of, the water-soluble vitamins and/or minerals.

DETAILED DESCRIPTION OF THE PREFERRED EMBODIMENTS

The present invention may be understood more readily by reference to the following detailed description of the preferred embodiments.

For purposes of clarity, various terms and phrases used throughout this specification and the appended claims are defined in the manner set forth below. If a term or phrase used in this specification, or in the appended claims, is not defined below, or otherwise in this specification, the term or phrase should be given its ordinary meaning

DEFINITIONS

The phrase "antioxidant agent" as used herein means an agent that is edible, and that can prevent or reduce an oxidation, degradation and/or other decomposition that would otherwise occur to components or ingredients of the compositions of the invention, such as water-soluble vitamins, minerals and/or edible oils. Antioxidant agents include, but are not limited to, ascorbyl palmitate, various tocopherol mixtures, acids, such as citric acid and ascorbic acid, herbal extracts, such as a Rosemary, Sage, Oregano, Ginger, Marjoram or Rosemary Oleoresins extract, plant phenols, such as Vanillin, ellagic acid and Resveratrol, and synthetic antioxidants, such as tertiary butylhydroquinone (TBHQ), butylated hydroxyamisole (BHA) or butylated hydroxytoluene (BHT), or mixtures thereof.

The phrase "Daily Reference Value" (DRV) as used herein means a label reference value set by the U.S. Food and Drug Administration ("FDA") for use in declaring the nutrient content of a food on its label or labeling.

The phrase "Daily Value" (DV) as used herein means a value set by the FDA for assisting consumers in understanding the relative significance of information about the amount of certain water-soluble vitamins and/or minerals in a food in the context of a total daily diet. This value assists consumers in comparing the nutritional values of food products. The Daily Value is determined by the FDA by combining the Reference Daily Intakes (RDIs) and the Daily Reference Values (RDAs) label reference values. The term "Daily Value," thus, refers to the combined set of label reference values.

The term "edible" as used herein means capable of being eaten, consumed and/or ingested by a mammal without being toxic or otherwise harmful to the mammal or, if the mammal is pregnant or lactating, to a developing fetus or a breast-feeding baby of the mammal.

The phrase "edible oils" as used herein means oils, or components thereof, such as fatty acids, that are edible, and that may be employed in pharmaceutical or other compositions for an oral administration. Edible oils include, but are not limited to, vegetable oils, including, Evening Primrose oil, Black Currant seed oil, Borage oil, Borage seed oil, safflower oil, safflower seed oil, sunflower oil, sunflower seed oil, sesame seed oil, peanut oil, walnut oil, almond oil, olive oil, olive seed oil, avocado oil, avocado seed oil, pumpkin seed oil, corn oil, cod liver oil, soy oil, soybean oil, coconut oil, palm oil, palm kernel oil, rapeseed oil, flaxseed (linseed) oil, cotton seed oil, tung oil, palmolein oil, mustard seed oil, oiticica oil and castor oil, and marine oils (including "fish oils"), such as those that are obtained from aquatic life forms, either directly or indirectly, particularly oily fish and components thereof, and combinations thereof. Other edible oils are known by those of skill in the art. A wide variety of edible oils are commercially available from sources known by those of skill in the art.

The phrase "effective amount" and "in an amount that is effective for" as used herein in connection with one or more vitamins, minerals, edible oils and/or compositions means an amount of the one or more vitamins, minerals, edible oils and/or compositions that is effective to provide, or enhance, a nutritional, health and/or medical benefit to a mammal, such as a human being. Using the information that is provided herein, and information that is known, those of ordinary skill in the art can readily determine an amount of one or more vitamins, minerals, edible oils and/or compositions that would be effective for providing, or enhancing, a nutritional, health and/or medical benefit to a wide variety of mammal under a wide variety of different nutritional, health or medical situations.

The phrase "essential fatty acids" as used herein means fatty acids that are necessary for mammals, but that are not synthesized by the body, for example, linoleic, linolenic and arachidonic acids.

The term "fat" as used herein means any of the various saturated and/or unsaturated (including monounsaturated and polyunsaturated), hydrogenated or unhydrogenated, soft solid, semisolid and/or solid organic compounds that generally comprise the glyceride esters of fatty acids and associated phosphatides, sterols, alcohols, hydrocarbons, ketones and/or related compounds, and includes components of fats, such as fatty acids, glycerides and ethyl esters containing fatty acids, or components thereof, and mixtures or other combinations of one or more fats. There is generally no chemical difference between fats and oils, with the only distinction being that fats are generally solid at room temperature and oils are generally liquid at room temperature. Components of fats and oils include, but are not limited to, fatty acids, glycerides (mono-, di- and tri-), ethyl and other esters of fatty acids, as well as components thereof and combinations thereof.

The phrase "fatty acids" as used herein means carboxylic acids that generally are derived from, or contained in, an animal, vegetable or other fat or oil, whether saturated, unsaturated, monounsaturated, polyunsaturated, aromatic, essential, nonessential, in a cis or trans form, in the ethyl esters, mono-, di- or tri-glycerides, free fatty acids or other forms, and components and combinations of the foregoing. Fatty acids include, but are not limited to, omega-3 fatty acids, omega-6 fatty acids and omega-9 fatty acids, and the specific fatty acids identified below:

| FATTY ACIDS | | | |
|---|---|---|---|
| Common Name | Number of Carbon Atoms | Number of Double Bonds | Fat or Oil Source |
| Butyric Acid | 4 | 0 | Butterfat |
| Caproic Acid | 6 | 0 | Butterfat |
| Caprylic Acid | 8 | 0 | Coconut Oil |
| Capric Acid | 10 | 0 | Coconut Oil |
| Lauric Acid | 12 | 0 | Coconut Oil |
| 'Myristic Acid | 14 | 0 | Palm Kernel Oil |
| Palmitic Acid | 16 | 0 | Palm Oil |
| Palmitoleic Acid | 16 | 1 | Animal Fats |
| Stearic Acid | 18 | 0 | Animal Fats |
| Oleic Acid | 18 | 1 | Olive Oil |
| Linoleic Acid | 18 | 2 | Corn Oil |
| Alpha-Linolenic Acid (ALA) | 18 | 3 | Flaxseed (Linseed) Oil |
| Gamma-Linolenic Acid (GLA) | 18 | 3 | Borage Oil |
| Gadoleic Acid | 20 | 1 | Fish Oil |
| Arachidonic Acid (ARA or AA) | 20 | 4 | Liver Fats, Peanut Oil, Fish Oil |
| Eicosapentaenoic Acid (EPA) | 20 | 5 | Fish Oil |
| Behenic Acid | 22 | 0 | Rapeseed Oil |
| Erucic Acid | 22 | 1 | Rapeseed Oil |
| Docosahexaenoic Acid (DHA) | 22 | 6 | Fish Oil |
| Lignoceric Acid | 24 | 0 | Most Fats |

Other fatty acids are known by those of skill in the art. A wide variety of fatty acids are commercially available from sources known by those of skill in the art. Also, edible oils can be separated into their component fatty acids on a capillary column in a gas chromatograph, and the relative fatty acid contents measured. Additional information concerning fatty acids is readily available from the Fatty Acid Producer's Council (New York, N.Y.).

The phrase "fungal oil" as used herein means an oil that is derived or obtained from a fungal source, whether modified or unmodified, such as Mucor javanicus, either directly or indirectly. As used herein, the phrase "fungal oil" includes, but is not limited to, one or more individual components present in fungal oil, such as DHA, arachidonic acid or other fatty acids. A wide variety of fungal oils are commercially available from known sources, such as Martek Corp. (Columbia, Md.).

The phrase "hollow oral dosage forms" as used herein means dosage forms for oral administration, such as hard or soft gelcaps or other capsules, microcapsules or caplets (which include gelatin or some other suitable or conventional material, such materials are known by those of skill in the art), which have not yet been fully or partially filled with a substance, material or composition to be enclosed therein (i.e. which do not yet contain all of the substance or composition to be enclosed within the oral dosage forms).

The term "hydrogenation" as used herein means a chemical process by which hydrogen is added to unsaturated fatty acids to produce partially or fully hydrogenated oils. Hydrogenation converts unsaturated bonds in the oil into saturated bonds. Some of the double bonds may be eliminated, while others may be incompletely transformed. These double bonds may be transformed from the natural "cis" configuration to the "trans" configuration.

The term "mammal" as used herein means a member of the class Mammalia, and includes, but is not limited to, developing fetuses, human beings (babies, infants, children, adults, pregnant woman, lactating women, women having childbearing potential that are attempting to become pregnant and the like) and animals.

The phrase "marine oil" as used herein has the meaning described above, and includes, but is not limited to, "fish oil" and one or more individual components of marine oil, such as an omega-3 fatty acid, including DHA, EPA, ALA, or a combination thereof. Marine oils include, for example, herring oil, cod oil, anchovy oil, tuna oil, sardine oil, menhaden oil and algae oil. Aquatic lifeforms that are employed to produce marine oils include, for example, farm-raised or wild, fresh-water or salt-water, fish and shellfish, such as herring, salmon, salmonoids, gadoids, shrimp, cod, carp, tilapia, perch, trout, sturgeon, krill, tuna, flat fish, anchovies, sardines, menhaden, shrimp, eels and seals. Marine oils may also be obtained from marine organisms, such as calanus (Calanus finmarchicus), a 3-4 mm copepod, algae and microalgae, for example, diatoms and dinoflagellates.

The term "medicament" as used herein means a substance or agent that promotes a recovery from an injury, illness, disease or disorder (i.e., that improves the medical condition of the mammal).

The term "minerals" as used herein means minerals that are edible, and includes those in an elemental, salt or other form. Examples of minerals include, but are not limited to, calcium, copper, fluorine, iodine, iron, magnesium, manganese, molybdenum, potassium, phosphorous, selenium and zinc, in an elemental form, or in the form of carbonates, oxides, phosphates, silicates, sulfates, sulfides or other forms. Many minerals are inorganic compounds that are necessary for life and good nutrition, such as calcium, copper, iron, magnesium, potassium and zinc. Additional information about minerals, including an extensive list of minerals, is present at the web site http://en.wikipedia.org/wiki/Minerals.

The term "nutrient" as used herein means an agent, substance or composition that is preferably soluble in water and insoluble in oil, and that is beneficial to the growth, development and/or health of a mammal, or that provides or enhances a nutritional, medical and/or other health benefit to a mammal, and includes, but is not limited to, vitamins, minerals, medicaments and other active agents.

The term "oil" as used herein means a fat that generally is viscous, liquid or liquefiable at room temperature, and includes mixtures and other combinations of one or more oils and/or components of oils, such as fatty acids, glycerides and/or ethyl esters of fatty acids (or components thereof). Oils may be derived or obtained from animal, marine, algae, fungal, mineral, plant (including vegetables and plant seeds), fruit, nut, synthetic or other sources, and are generally composed largely of glycerides of the fatty acids, particularly oleic, palmitic, stearic and linolenic. Oils may be hydrogenated or non-hydrogenated, and saturated or unsaturated (including monounsaturated and polyunsaturated). Plant sources of oil include, but are not limited to, hydrogenated and non-hydrogenated vegetable oils and plant seed oils, Evening Primrose oil, Black Currant seed oil, Borage oil, Borage seed oil, safflower oil, safflower seed oil, sunflower oil, sunflower seed oil, sesame seed oil, peanut oil, olive oil, olive seed oil, corn oil, avocado oil, avocado seed oil, pumpkin seed oil, soy oil, soybean oil, coconut oil, palm oil, palm kernel oil, rapeseed oil, flaxseed (linseed) oil, cotton seed oil, tung oil, oiticica oil and castor oil. Examples of fats derived from marine sources include fish oil and algae oil. Other oils are known by those of skill in the art. A wide variety of oils are commercially available from sources known by those of skill in the art.

The phrase "oral dosage forms" as used herein means dosage forms for an oral administration, such as hard or soft gel or other capsules, microcapsules and caplets, and the like. Such oral dosage forms may include in their outer structure gelatin or some other suitable or conventional material. Such materials are known by those of skill in the art.

The phrase "plant seed oil" as used herein means an oil that is extracted or otherwise obtained from a seed of a plant, either directly or indirectly, particularly oily seeds, including one or more individual components thereof and mixtures thereof. Plant seed oils include, but are not limited to, Black Currant seed oil, Borage seed oil, safflower seed oil, sunflower seed oil, sesame seed oil, avocado seed oil, pumpkin seed oil, olive seed oil, coconut seed oil, rapeseed oil, flaxseed (linseed) oil, cottonseed oil and tung oil. Other plant seed oils are known by those of skill in the art.

The phrase "plant oil" as used herein means an oil that is extracted or otherwise obtained from a plant, either directly or indirectly, particularly oily plants, including one or more individual components thereof and mixtures thereof. Plant oils include, but are not limited to, Evening Primrose oil, Borage oil, safflower oil, sunflower oil, peanut oil, walnut oil, almond oil, avocado oil, olive oil, corn oil, soy oil, soybean oil, coconut oil, palm oil, palm kernel oil and castor oil. Other plant oils are known by those of skill in the art.

The term "plurality" as used herein means more than one, such as two, three, four, five, six, seven, eight, nine, ten, fifteen, twenty or the like.

The phrase "Reference Daily Intakes" (RDIs) as used herein means a label reference value set by the FDA for use in declaring the nutrient content of a food on its label or labeling. The FDA has replaced label reference values created in 1973 that are known as "U.S. Recommended Daily Allowances" (U.S. RDAs) with RDIs.

The phrases "solid-state" and "solid-state form" as used herein mean having a form that is a soft solid, a semisolid or a solid (i.e. not liquid) including size-reduced solids, for example, powders, granules and milled materials. Methods are known by those of skill in the art for size reducing solid particles, such as milling, grinding, cutting and like methods.

The phrase "suspending agent" as used herein means a substance, material or composition that is edible, and that has an ability to initiate, permit, promote, enhance or maintain a suspension of one or more soft-solid, semi-solid or solid components in a semi-liquid or liquid vehicle. Examples of suspending agents include, for example, lecithin, and yellow beeswax.

The term "suspension" as used herein means an incorporation of one or more solid-state components into a semi-liquid or liquid vehicle, and includes colloidal and other types of suspensions. Preferably, the suspension is a uniform suspension (i.e. the components are uniformly present in a semi-liquid or liquid vehicle). If the particle sizes of the component particles are larger than colloidal dimensions (i.e., they are not small enough to pass through filter membranes), the component particles may have a tendency to precipitate (if they are heavier than the suspending medium) or agglomerate and rise to the surface (if they are lighter than the suspending medium). In both cases, the component particles may "settle out" of the suspension.

The phrase "temporarily suspended" as used herein in connection with one or more water soluble vitamins and/or minerals and one or more edible oils means that the one or more water soluble vitamins and/or minerals are partially or fully, and preferably fully, suspended in the one or more edible oils for a period of time that is sufficient to permit the one or more water soluble vitamins and/or minerals and the one or more edible oils preferably to be uniformly inserted into two or more hollow oral dosage forms, such as hollow gel capsules, gelcaps, or caplets (i.e., in a manner that the same or similar amount of the one or more vitamins, minerals and/or edible oils becomes inserted into the two or more hollow oral dosage forms). Such a period of time may vary depending upon a wide variety of factors, such as the numbers and types of the water-soluble vitamins and/or minerals and edible oils being employed, the number of hollow oral dosage forms being filled and the like, and can readily be determined by those of skill in the art.

The phrase "uniformly inserted into" when used herein in connection with one or more water-soluble vitamins and/or minerals, one or more edible oils and hollow oral dosage forms means that approximately the same quantities of the one or more water-soluble vitamins and/or minerals and the one or more edible oils are generally placed into each of the hollow oral dosage forms being filled (whether they are being partially or completely filled). For example, if one hundred hollow soft gel capsules, gelcaps, or caplets are being filled with one or more edible oils having one or more water-soluble vitamins and/or minerals suspended therein, approximately the same quantities of the one or more water-soluble vitamins and/or minerals and the one or more edible oils will generally be present in each of the soft gel capsules, gelcaps, or caplets after the filling operation.

The phrase "unit dosage form" as used herein means one individual dosage form for an oral administration to a mammal, such as one hard gel capsule containing a composition of the invention.

The term "vitamin B6" means know chemical forms of vitamin B6 including, but not limited to pyridoxine, pyridoxamine, and pyridoxal.

The term "vitamin B9" means folic acid folate or one or more natural isomers of reduced folate, including but not limited to L-methylfolate, L-5-methyl-tetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-forminino-(6S)-tetrahydrofolic acid, (6S)-5-methyl-tetrahydrofolic acid and polyglutamyl derivatives of tetrahydrofolate acid.

The term "vitamin B12" means known chemical forms of vitamin B12 including, but not limited to cyanocobalamin, cobalamin, and reduced forms of cobalamin, and also includes all forms both bound and unbound to recombinant intrinsic factor.

The phrase "without being degraded" as used herein in connection with water-soluble vitamins, minerals and/or edible oils means that no degradation, or substantially no degradation, preferably occurs. When substantially no degradation occurs, some minimal degradation may still occur, but the amount of such degradation is generally insufficient to prevent or reduce the nutritional, medical or other health benefits provided by the nutrient or edible oil to the mammal.

The phrase "water-soluble" as used herein in connection with water-soluble vitamins and/or minerals means that the vitamins and/or minerals dissolve partially or fully (and preferably fully) in water, and preferably form an equilibrium concentration of at least about 0.001 mg/mL at 25° C.

Edible Oils

Any one or more of a wide variety of edible oils, or combinations thereof, may be employed in the compositions of the invention, including, but not limited to, those specifically discussed herein. Because of the nutritional, medical and/or other health benefits that they can provide to mammals, edible oils that are preferred for use in the compositions of the invention are those that are, or are rich in (contain large quantities of), essential fatty acids, omega-3 fatty acids, omega-6 fatty acids and/or omega-9 fatty acids, particularly DHA, EPA, ARA, AA, ALA or GLA, ocosapentaenoic acid, eicosatetraenoic acid, moroctic acid, heneicosapentenoic acid, gamma-linolenic acid, linoleic acid, arachidonic acid and oleic acid. As a result of an enhanced stability, such such fatty acids are preferably present in their ethyl esters or tryglycerides forms. The most preferred edible oils for use in the compositions of the invention are those that are, or are rich in, omega-3 fatty acids and/or essential fatty acids, such as DHA.

The edible oils that may be employed in the compositions of the invention are commercially available from sources known by those of skill in the art. Sources for these edible fats and oils include, for example, Martek Corp. (Columbia, Md.), Ocean Nutrition Canada, Ltd. (Bedford, Nova Scotia, Canada), DSM (Heerlen, NL), Pronova Biocare AS (Lysakar, Norway), Napro AS (Brattvaag, Norway), Berg Lipotech AS (Norway), ADM Food Oils (Decatur, Ill.), and Oilseeds International, Ltd. (San Francisco, Calif.).

Edible oils, such as omega-3 marine oils, are generally commercially available in the ethyl esters, triglycerides or free fatty acids forms. The ethyl esters form of edible oils result from breaking apart the original triglyceride molecules through the known process of "ethylation," which is performed to increase or concentrate the level of omega-3 fatty acids, while removing the less desirable fatty acids. Ethyl esters of EPA and DHA are available from DSM (Heerlen, NL) under the name Ropufa® 75 n-3 EE, and from other oil suppliers described herein.

The triglycerides form of edible oils generally consists either of an unconcentrated fish oil (about 18% EPA and about 12% DHA), or of a concentrated fish oil that has been reconverted (re-esterified) back to the tri-glycerides form. In the processing of marine and other edible oils, the objective is generally to remove existing free fatty acids, monoglycerides and diglycerides to form more stable compositions of the fatty acids, which is the triglycerides or ethyl esters forms of the fatty acids.

The fatty acids form of edible oils generally results from saponification and neutralization of the triglycerides, using known techniques, whereby the glycerol backbone of the triglycerides is generally severed, leaving only the free fatty acid form. Such processing techniques preferably result in the edible oils having an acid value below about 5.0 mg KOH/g and unsaponified matter below about 1.5% w/w.

Methods are also known by those of skill in the art for extracting oil from fish. For example, raw fish can be placed into a cooker and heated to a temperature of about 95°. This temperature can be reached by heating the fish meat directly, or indirectly, with steam. Such heating aids in the coagulation of proteins in the fish meat. As the proteins coagulate, the heating also helps recover fat and water from the fish meat. The cooked fish meat can be collected and conveyed to screw presses, which aid in the removal of any remaining oil and/or water from the fish. The resulting liquid, which is called "pressliquor," undergoes a series of known decanting and separating techniques. Decanters are employed to separate solid fish meat from the liquid. The pressliquor can be pumped into cylindrical bowls and conveyers to rotate. The rotation of the decanter helps to force the solids to the outside of the bowl, where they are collected. The remaining liquid continues through the process. After decanting, the pressliquor can be pumped through a separator. A high-speed rotation of separator plates results in the separation of the oil from the water, resulting in a fish oil. Marine oil can be extracted from aquatic lifeforms other than fish in a similar manner. All of the equipment and techniques employed in extracting marine oil from fish and other aquatic lifeforms are known and/or commercially available.

Methods are also known by those of skill in the art for extracting oil from seeds, including the known solvent extraction and mechanical extraction (cold processing) methods.

Oils that are extracted from fish, plants and other sources may have a pronounced color, flavor and aroma. If the refining of such oils does not cause the amount of water-soluble vitamins and/or minerals present therein to be reduced or eliminated, it is, thus, preferable that edible oils that are employed in the compositions of the invention, and that are extracted from such sources, be refined, deodorized and substantially free of fish meat, flesh, seeds or other solids. Such refinement methods are known by those of skill in the art, and generally result in a clean, "finished" oil product. When some oils, such as Evening Primrose oil, are refined, however, water-soluble vitamins or minerals present in the oils are significantly reduced by the refinement process. Those of skill in the art know which edible oils have their water-soluble vitamins or minerals reduced by refinement processes. Unrefined oils are sometimes referred to as "virgin" or "extra virgin" oils.

Marine (and other) oils employed in the methods of the invention may preferably be refined and deodorized using methods known in the art. For example, methods for processing marine and other edible fats and oils are described in "Fish Oils: Their Chemistry, Technology, Stability, Nutritional Properties and Uses" (The Avi Publishing Company, Inc., 1967); Marschner et al. U.S. Pat. No. 4,804,555, entitled "Simultaneous Deodorization and Cholesterol Reduction of Fats and Oils;" and A. P. Bimbo, "Production of Fish Oil," Fish Oils in Nutrition, Chapter 6, 141-180 (M. E. Stansby ed., New York, Van Nostrand Reinhold); the disclosures of which are expressly incorporated by reference herein.

Both physical refining and chemical refining can generally be employed to refine oils that can be employed in compositions for oral administration. Physical methods include the known filtering, deodorizing and winterization processes. Chemical methods include the known degumming, neutralization and bleaching processes. Additional information concerning the refinement of oils for use in compositions for oral administration is present at the web site www.sanmarkltd.com/processing.htm.

Marine oil purification is a process in which crude oils are refined to remove fish meat and flesh, as well as other substances that may contribute to off flavor, off odor, undesirable color or keeping quality. The oils can be purified, or fatty acids can be removed from the oils, by degumming the oils (by washing the oils generally using water, salts and acids in order to remove waxes, phosphates and other impurities therefrom). After the impurities are removed from the oils through degumming, the oils can undergo a neutralization process. Alkali can be mixed with the oils to remove free fatty acids, which can contribute to rancidity. A resulting soap/oil mixture can be heated to, for example, 180° F., and pumped through a separator that removes the soap from the oil.

After the above "chemical" refinements have been made, the oils can be subjected to "physical" refinements. The first of these physical refinements is generally the removal of odor compounds from the oils. This can be accomplished by applying a vacuum steam distillation process to the oils. Steam distillation can be followed by winterization, which involves a cooling of the oils. As a result of this cooling process, some oils become crystallized, and can thereafter be removed from other oils using filtration techniques. This results in the oils being more uniform. After winterization, the oils can be bleached and hydrogenised, which processes can stabilize the oils. Bleaching involves the use of clay to remove color and impurities from the oils. The oils can be bleached by heating, for example, to about 130° F., and mixing them with clay. The mixture can be held for several minutes, and then the hot oil can be filtered from the clay and cooled. Hydrogenation can be completed, following bleaching, by pumping pressurized hydrogen into an agitated tank filled with the oils. This is generally done in the presence of a catalyst metal, such as nickel. Hydrogenation can be performed at a temperature, for example, of about 204° C., and a pressure of, for example, 60 psig.

Similar known methods to those described above can be employed with other types of edible oils. Further, other methods known by those of skill in the art can also be employed to purify marine and other types of edible oils, or to remove fatty acids from such oils. Methods for processing marine and other edible fats and oils are well known in the art. (See, for example, "Fish Oils: Their Chemistry, Technology, Stability, Nutritional Properties and Uses" (The Avi Publishing Company, Inc., 1967); Marschner et al. U.S. Pat. No. 4,804,555, entitled "Simultaneous Deodorization and Cholesterol Reduction of Fats and Oils;" A. P. Bimbo, "Production of Fish Oil," Fish Oils in Nutrition, Chapter 6, 141-180 (M. E. Stansby ed., New York, Van Nostrand Reinhold).

In order to permit edible oils employed in the compositions of the invention to provide maximum nutritional, health and/or medical benefits, it is preferred that the edible fats and oils not be hydrogenated. As discussed hereinabove, the hydrogenation of marine or other edible oils by decreasing polyunsaturation, including n-3 fatty acid components, generally correspondingly decreases the health value of such oils.

In the United States, there are currently no Reference Daily Intakes (RDIs), Daily Reference Values (DRVs) or Daily Values (DVs) for essential fatty acids or other edible oils. However, the World Health Organization recommends that pregnant and lactating women consume 5% of their daily caloric intake as essential fatty acids. It is recommended that healthy adults consume 4% to 10% of their daily caloric intake as essential fatty acids.

The amount of one or more edible oils that may be included in the compositions of the invention is an amount that is preferably effective for providing or enhancing some nutritional, health, medical or other benefit to the mammal, and that is not harmful to the mammal.

DHA may, for example, optionally be included as a component of the compositions of the invention in an amount that is effective for providing, or increasing the supply of DI-LA to developing fetuses or babies through, for example, placentas or breast milk, or to other mammals, and that is not harmful to developing fetuses or breast-feeding babies, or to other mammals. The amount of DHA that is preferably present in these compositions ranges from about 0.05 to about 3 weight percent of the total weight of the compositions, and more preferably ranges from about 0.2 to about 0.6 weight percent, with about 0.3 weight percent being most preferred (for pregnant women, lactating women, and women having childbearing potential that are attempting to become pregnant, or for other mammals).

Edible oils are susceptible to oxidation, degradation and decomposition, particularly when they are exposed to oxygen (present in the air or otherwise), or when they are in contact with substances that initiate or catalyze (accelerate the rate of) the oxidation, degradation and/or other decomposition of edible oils, such as free radicals or certain minerals. Free radicals are highly reactive molecular fragments that have one or more unpaired electrons and generally act as initiators or intermediates in oxidation reactions. Minerals, particularly copper, iron, magnesium, manganese, molybdenum and zinc, generally catalyze an oxidation and/or degradation of edible oils. Those of skill in the art know which vitamins, minerals and other water-soluble vitamins initiate or catalyze the oxidation, degradation and/or other decomposition of edible oils. It is, thus, preferred that the compositions of the invention comprise vitamins, minerals and other water-soluble vitamins and/or minerals that do not initiate or catalyze an oxidation, degradation or other decomposition of edible oils.

The amount of oxidation, degradation and decomposition that occurs to an edible oil, or to a composition containing one or more edible oils, can be determined by tests known by those of skill in the art. The most commonly used measure for testing an oxidation of an edible fat or oil, or of a solid or liquid food product containing one or more edible fats or oils, is the Peroxide Value Test, which measures the concentration of the immediate products of oxidation (peroxides). However, these initial peroxide products are themselves degraded over time to various aldehydes, and these aldehyde secondary products are not detected by the Peroxide Value Test. A second known test, the Anisidine Test, may be used to detect the secondary products. Thus, the Peroxide Value Test measures the degree to which oxidation is taking place at the present moment, and the Anisidine Test measures the amount of historical oxidation over the life of a edible fat, oil or food product. These two measures may be combined to give a total oxidation (or TOTOX) value, which is calculated as:

TOTOX=Anisidine Value+(2×Peroxide Value).

Known organoleptic testing procedures can also be employed to test the taste and smell of edible fats and oil, and food products containing one or more edible fats and/or oils.

Edible oils include vegetable-based oils, such as soybean, corn, cottonseed, peanut, safflower, sunflower, canola and olive oil. In addition, edible oils include marine oils (including "fish oils"), such as those that are obtained from aquatic lifeforms, either directly or indirectly, particularly oily fish. Marine oils generally contain high levels of omega-3 fatty acids. Marine oils having a total omega-3 fatty acid content of greater than about 5 weight percent include those derived from menhaden oil, herring, capelin, anchovy, cod liver, salmon oil, sardine oil and mixtures thereof.

As those of skill in the art will appreciate, any one or more of a wide variety of edible fats and/or oils, and preferably those that contain omega-3 fatty acids, including DHA and/or EPA, may be employed in the compositions and methods of the present invention, including, but not limited to, the marine oils, fungal oils, plant oils and plant seed oils and combinations thereof. Edible fats and oils that are preferred for use in the methods of the invention are those that are rich in omega-3 fatty acids, such as DHA. The most preferred edible fats and oils for use in the methods of the invention are those containing at least about 5 percent by weight DHA, more preferably from about 10 percent by weight DHA to about 80 percent by weight DHA and most preferably about 20 percent by weight DHA to about 70 percent by weight DHA. DI-1A may be independently isolated and added to an omega-3 oil, or an omega-3 oil may be otherwise enriched in DHA content as is known in the art. Omega-3 oils additionally or alternatively may contain amounts of other omega-3 fatty acids, such as EPA.

Vitamins and Minerals

A wide variety of oil and/or water-soluble vitamins, minerals, and combinations thereof, may be used in the methods and compositions of the invention in varying quantities.

A primary aspect of the invention is that water soluble vitamins and/or minaerals will be present in the compositions. However, it is also contemplated that soluble vitamins and minerals can be present in addition to the, or alternatively to, water soluble vitamins and/or minerals. The oil soluble vitamins and/or minerals can be dissolved in one or more edible oils or be present in its own phase or mixtures thereof. Oil soluble vitamins and/or minerals can, optionally, be added to one or more other edible oils or may be naturally occurring in one or more edible oils.

Water soluble vitamins and minerals that can be used in the methods and compositions of the invention include, but are not limited to, Vitamin B1 (as Thiamin or Thiamine Mononitrate), Vitamin B2 (as Riboflavin), Vitamin B3 (as Niacin), Vitamin $B_6$ (as Pyridoxine or Pyridoxine Hydrochloride), Vitamin B9/M (Folic Acid or Folate) or of reduced Folate, including but not limited to L-methylfolate, L-5-methyltetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, and polyglutamyl derivatives of tetrahydrofolate acid, Vitamin B12 (cyanocobalamin, cobalamin, and reduced forms of cobalamin), Biotin, Vitamin C (Ascorbic Acid), Folacin, Niacinamide, Calcium (as Calcium Carbonate), Iron (as Ferrous Fumarate), Phosphorus, Pantothenic Acid (as Calcium Pantothenate), Iodine (as Potassium Iodide), Magnesium (as Magnesium Oxide), Zinc (as Zinc Oxide), Selenium (as Sodium Selenate), Copper (as Cupric Oxide), Manganese (as Manganese Sulfate), Chromium (as Chromium Chloride), Molybdenum (as Sodium Molybdate), Choline, Fluoride, Chloride, Potassiuin, Sodium, Biotin and various mixtures or other combinations thereof. L-methylfolate, or Metafolin™ (Merck-Eprova AG Schaffhausen, Switzerland), may also be used in place of or in addition to folic acid or folate. Recombinant Intrinsic Factor (rhIF) with bound Cobalamin (Cobento Biotech A/A, Science Park, Aarhus, Denmark) may be used in place of or in addition to vitamin B12.

Recombinante Intrinsic Factor is thought to be vital for the transport of vitamin B12 within the body. Intrinsic factor is normally present in the stomach. More specifically it is a glycoprotein secreted by parietal (humans) cells of the gastric mucosa. In humans, it has an important role in the absorption of vitamin B12 in the intestine.

Oil soluble vitamins and minerals that may be employed in the methods and compositions of the invention include, but are not limited to, Vitamin A, Vitamin D, Vitamin E (as dl-Alpha Acetate or d-alpha Nat'l), Vitamin K and Tocopherol.

Compositions of the invention may be formulated using any pharmaceutically-acceptable forms of the vitamins and/or minerals described above, including their salts, which are known by those of skill in the art. For example, useful pharmaceutically-acceptable calcium compounds include any of the well-known calcium supplements, such as Calcium Carbonate, Calcium Sulfate, Calcium Oxide, Calcium Hydroxide, Calcium Apatite, Calcium Citrate-Malate, Bone Meal, Oyster Shell, Calcium Gluconate, Calcium Lactate, Calcium Phosphate, Calcium Levulinate, and the like. Pharmaceutically-acceptable magnesium compounds include Magnesium Stearate, Magnesium Carbonate, Magnesium Oxide, Magnesium Hydroxide and Magnesium Sulfate. Pharmaceutically-acceptable iron compounds include any of the well-known Iron II (ferrous) or Iron III (ferric) supplements, such as Ferrous Sulfate, Ferric Chloride, Ferrous Gluconate, Ferrous Lactate, Ferrous Tartrate, Iron-Sugar-Carboxylate complexes, Ferrous Fumarate, Ferrous Succinate, Ferrous Glutamate, Ferrous Citrate, Ferrous Pyrophosphate, Ferrous Cholinisocitrate, Ferrous Carbonate, and the like. The vitamins and/or minerals that may be included in compositions of the invention may be microencapsulated in a coating of fat, microcrystalline cellulose or similar material in order to prevent their degradation under various conditions.

The vitamins and/or minerals that are preferred for use in the methods and compositions of the invention are those that have Daily Values (DVs), Reference Daily Intakes (RDIs) and/or Daily Reference Values (DRVs) described by the U.S. Food and Drug Administration (FDA) in its regulations or publications, such as the Code of Federal Regulations or Federal Register, Vol. 58, No. 3 (1993), for the following five categories of persons: (1) infants (persons not more than 12 months of age); (2) children under 4 years of age (persons 13 through 47 months of age); (3) adults and children that are 4 or more years of age; (4) pregnant women; and (5) lactating women. The most preferred vitamins and/or minerals for use in the methods and compositions of the invention are vitamin B6, vitamin B9 and vitamin B12.

One or more vitamins and/or minerals may be employed in the compositions of the invention in any quantity that is effective for providing, or enhancing, a nutritional, medical and/or other health benefit to a particular mammal, and that is safe for consumption by the particular mammal, such as pregnant women, lactating women or women having childbearing potential that are attempting to become pregnant or their developing fetuses or babies (i.e., a quantity that would not cause harm to a woman consuming the composition, or to her developing fetus or breast-feeding baby). This quantity may vary depending upon the particular vitamins and/or minerals chosen for use, the age, size, weight and health condition of the mammal and like considerations, but generally ranges from about 2.5 to about 50 weight percent of the total weight of the compositions, and more preferably ranges from about 5 to about 25 weight percent, with about 10 weight percent being most preferred. The DVs described by the FDA, for example, in Federal. Register, Vol. 58, No. 3 (1993) or in 21 CFR 101.9, for the different categories of human beings described above may be employed to determine such quantity for different mammals, and are set forth below.

DAILY VALUES

| | Units | Infants | Children Under 4 Years | Pregnant Women | Lactating Women | Persons that are 4 Years or Older |
|---|---|---|---|---|---|---|
| Vitamins | | | | | | |
| Vitamin A | IU | 1,500 | 2,500 | 8,000 | 8,000 | 5,000 |
| Vitamin C | mg | 35 | 40 | 60 | 60 | 60 |
| Vitamin D | IU | 400 | 400 | 400 | 400 | 400 |
| Vitamin E | IU | 5 | 10 | 30 | 30 | 30 |
| Vitamin K | μg | *** | *** | *** | *** | 80 |
| Vitamin B1 | mg | 0.5 | 0.7 | 2.5 | 2.5 | 1.5 |
| Vitamin B2 | mg | 0.6 | 0.8 | 2.0 | 2.0 | 1.7 |
| Vitamin B3 | mg | 8. | 9 | 20 | 20 | 20 |
| Vitamin B6 | mg | 0.4 | 0.7 | 2.5 | 2.5 | 2.0 |
| Vitamin B9 | mg | 1 | 0.2 | 0.8 | 0.8 | ** |
| Folate * | mg | *** | *** | *** | *** | 0.4 |
| Vitamin B12 | μg | 2 | 3 | 8 | 8 | 6 |
| Biotin | mg | 0.05 | 15 | 0.3 | 0.3 | 0.3 |
| Minerals | | | | | | |
| Pantothenic Acid | mg | 3 | 5 | 10 | 10 | 10 |
| Calcium | g | 0.6 | 0.8 | 1.3 | 1.3 | 1 |
| Phosphorus | g | 0.5 | 0.8 | 1.3 | 1.3 | 1 |
| Iodine | μg | 45 | 70 | 150 | 150 | 150 |
| Iron | mg | 15 | 10 | 18 | 18 | 18 |
| Magnesium | mg | 70 | 200 | 450 | 450 | 400 |
| Copper | mg | 0.6 | 1.0 | 2.0 | 2.0 | 2.0 |
| Zinc | mg | 5 | 8 | 15 | 15 | 15 |
| Selenium | μg | *** | *** | *** | *** | 70 |
| Manganese | mg | *** | *** | *** | *** | 2.0 |
| Chromium | μg | *** | *** | *** | *** | 120 |
| Molybdenum | μg | *** | *** | *** | *** | 75 |
| Chloride | mg | *** | *** | *** | *** | 3,400 |

* Folate is the anion form of folic acid (currently known as folacin or Vitamin B9 and formerly known as vitamin M). Vitamin B9 can be present as folic acid or one or more natural isomers of reduced Folate, including but not limited to L-methylfolate, L-5-methyltetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid and polyglutamyl derivatives of tetrahydrofolate.
** Information not present in 21 CFR 101.9.
*** Information not present in Federal Register, Vol. 58, No. 3 (1993).

\*—Folate is the anion form of folic acid (currently known as folacin or Vitamin B9 and formerly known as vitamin M). Vitamin B9 can be present as folic acid or one or more natural isomers of reduced Folate, including but not limited to L-methylfolate, L-5-methyltetrahydrofolate, L-5-methyl-tetrahydrofolic acid, (6S)-tetrahydrofolic acid, (6S)-5-methyl-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid and polyglutamyl derivatives of tetrahydrofolate.

\*\*—Information not present in 21 CFR 101.9.

\*\*\*—Information not present in Federal Register, Vol. 58, No. 3 (1993).

Additional information is available at www.nal.usda.gov.

It is important that the quantity of each vitamin and/or mineral used in a method or composition of the invention be safe for consumption by pregnant women, lactating women or women having childbearing potential that are attempting to become pregnant, and is safe for their developing fetuses or babies, or is safe for consumption by other mammals that consume the composition. Larger quantities of certain vitamins and/or minerals may cause damage to a developing fetus or baby, or to other mammals. Those of skill in the art know the quantities of vitamins and minerals above the U.S. DVs for pregnant women, lactating women or women having childbearing potential that are attempting to become pregnant, or for other mammals, that would be harmful for the mammal consuming the composition, or for their developing fetuses or babies.

Set forth hereinbelow are the approximate preferred ranges of the daily quantities of the various vitamins and minerals that may generally be used in one composition of the invention (or divided between more than one composition of the invention for consumption during a one-day period) for mammals, including pregnant women, lactating women or women having childbearing potential that are attempting to become pregnant (from about one quantity to about another quantity), as well as more preferred ranges, and the most preferred quantities for pregnant and lactating women.

PREFERRED RANGES

| | Units | More Preferred Range | Most Preferred Range | Most Preferred Quantity for Pregnant Women | Quantity for Lactating Women |
|---|---|---|---|---|---|
| Vitamin | | | | | |
| Vitamin A | IU | 0-9,000 | 1,500-8,000 | 8,000 | 8,000 |
| Vitamin C | mg | 0-1,000 | 35-500 | 60 | 60 |
| Vitamin D | IU | 0-800 | 200-400 | 400 | 400 |
| Vitamin E | IU | 0-1,500 | 5-400 | 30 | 30 |
| Vitamin K | µg | 0-80 | 10-80 | 10 | 10 |
| Vitamin B1 | mg | 0-50 | 0.5-10 | 2.5 | 2.5 |
| Vitamin B2 | mg | 0-50 | 0.5-25 | 2.0 | 2.0 |
| Vitamin B3 | mg | 0-60 | 5-40 | 20 | 20 |
| Vitamin B6 | mg | 0-50 | 0.4-30 | 2.5 | 2.5 |
| Vitamin B9 | mg | 0-2 | 0.2-1.0 | 0.8 | 0.8 |
| Vitamin B12 | µg | 0-1,000 | 2.0-18 | 8 | 8 |
| Biotin | mg | 0-15 | 0.05-15 | 0.3 | 0.3 |
| Mineral | | | | | |
| Pantothenic Acid | mg | 0-20 | 3-15 | 10 | 10 |
| Calcium | g | 0-3 | 0.2-2.0 | 1.3 | 1.3 |
| Phosphorus | g | 0-2 | 0.1-1.5 | 1.3 | 1.3 |
| Iodine | µg | 0-200 | 45-150 | 150 | 150 |
| Iron | mg | 0-100 | 5-50 | 18 | 18 |
| Magnesium | mg | 0-600 | 50-500 | 450 | 450 |
| Copper | mg | 0-2 | 0.1-2 | 2 | 2 |
| Zinc | mg | 0-30 | 1-25 | 15 | 15 |
| Selenium | µg | 0-400 | 60-100 | 60 | 70 |
| Manganese | mg | 0-5 | 0.1-5 | 5 | 5 |
| Chromium | µg | 0-150 | 0.1-120 | 25 | 25 |
| Molybdenum | µg | 0-75 | 20-75 | 25 | 25 |
| Chloride | mg | 0-3,400 | 2,000-3,400 | Not Established | Not Established |
| Choline | mg | 0-1,000 | 300-600 | 450 | 550 |
| Fluoride | mg | 0-5 | 1-4 | Not Established | Not Established |
| Potassium | mg | 0-80 | 10-80 | Not Established | Not Established |
| Sodium | mg | 0-2,400 | 10-1,000 | Not Established | Not Established |

One composition of the invention may contain one or more of the above (or other) vitamins and/or minerals in their preferred or other quantity range (or in their more preferred range, or in the most preferred quantity for pregnant women, lactating women or women having childbearing potential that are attempting to become pregnant, or for other mammals). Alternatively, one composition may contain each of these vitamins and/or minerals in one half, one third, one forth, one fifth, one sixth, and so forth, of these quantities. Varying combinations of a wide variety of vitamins and minerals may also be employed.

The compositions of the invention may contain any number, and any combination, of edible oils, such as essential and non-essential fatty acids. In a preferred embodiment of the invention, only one edible oil is present in the compositions, and the edible oil comprises a beneficial fatty acid, preferably an omega-3 fatty acid, such as docosahexanoic acid (DHA).

In this embodiment, the DHA content is about 45 to 70 weight percent. The DHA content of the compositions of the invention is preferably greater than about 5 weight percent of the total weight of the edible oils, and more preferably, greater than about 10 weight percent of the total weight of the edible oils, and still more preferably greater than about 25 weight percent of the total weight of the edible oils, such as a DHA content of about 50 weight percent of the total weight of the edible oils, or greater.

Vitamins and minerals are commercially available from sources known by those of skill in the art, such as Hoffmann-LaRoche Inc. (Nutley, N.J.). Additionally, vitamin A can be derived from dark green, dark yellow and orange vegetables, such as carrots and sweet potatoes and colored fruits, such as peaches, oranges, and apple. Vitamin B1 may be derived from wheat germ, nutritional yeast, cooked beans and peas, collard greens, raisins, oranges, nuts, and whole grains. Vitamin B2 may be derived from dark green leafy vegetables, avocado, wheat germ, and whole grains. Vitamin B3 (Niacin) may be derived from cooked dried beans and peas, nuts, whole wheat and grains, potato, and nutritional yeast. Vitamin B6 (Pyridoxine) may be derived from cooked dried beans and peas, nutritional yeast, wheat germ, nuts, bananas, avocados, leafy greens, cabbage, cauliflower, potatoes, whole grains, and dried fruit. Vitamin B7(Biotin) may be derived from oatmeal, nutritional yeast, legumes, soybeans, mushrooms, bananas, nuts, and whole grains. Vitamin B12 (cyanocobalamin, cobalamin, and/or reduced forms of cobalamin) may be derived from nutritional yeast, fortified foods and beverages such as cereals, soymilk and orange juice. Folate (Folic Acid) may be derived from dark green leafy vegetables, nutritional yeast, beans, avocados, wheat germ, various fruits like banana, orange, and whole grains. Pantothenic Acid may be derived from legumes, soybeans, avocados, mushrooms, green vegetables, bananas, oranges, whole grains and wheat germ. Vitamin C (Ascorbic Acid) may be derived from fresh fruits and vegetables, green pepper, broccoli, citrus fruits, tomatoes, guava and strawberries. Vitamin D may be derived from sunlight, fortified foods and beverages. Vitamin E (Tocopherol) may be derived from vegetable oils, seeds, nuts, wheat germ, spinach, peaches, avocados, broccoli, dried prunes and whole wheat. Vitamin K may be derived from green or leafy vegetables, broccoli, turnip greens, cabbage, cauliflowers and avocados.

Although a wide variety of vitamins and/or minerals may be employed in the methods and compositions of the invention, compositions of the invention preferably include vitamin B6, vitamin B9 and/or vitamin B12. Vitamin B6 (as Pyridoxine or Pyridoxine Hydrochloride) may, for example, be present in the composition in an amount that preferably ensures the presence of from at least about 1 mg to about 50 mg per unit dosage form. Vitamin B9/M (Folic Acid) may, for example, be present in the composition in an amount that preferably ensures the presence of from at least about 100 µg to about 1000 µg per unit dosage form. Vitamin B12 (cyanocobalamin, cobalamin, and/or reduced forms of cobalamin) may, for example, be present in an amount that preferably ensures the presence of from at least 200 µg to about 2000 µg per units dosage form. A variety of vitamins and minerals, including vitamin B6, vitamin B9 and vitamin B12 are commercially available from sources known by those of skill in the art, such as Hoffmann-LaRoche Inc. (Nutley, N.J.). Preferably, solid-state vitamins are provided as finely divided powders, such as amorphous powders or very finely milled crystalline powders. This generally ensures content uniformity and inhibits agglomeration of the vitamins and/or minerals in the compositions of the invention.

In addition to vitamins, minerals and edible oils, the compositions of the invention may contain one or more additional pharmaceutically acceptable compounds, drugs, substances, ingredients or materials.

Wetting agents, emulsifiers, lubricants, coloring agents, release agents, coating agents, sweetening agents, flavoring agents, preservatives, suspending agents, antioxidant agents, additional carriers and other suitable agents may also, optionally, be included within the compositions of the invention. However, such materials should be compatible with other ingredients that are present in the compositions, and not harmful to mammals.

Pharmaceutically acceptable antioxidants that may, optionally, be included in the compositions of the invention include, for example: (a) water soluble antioxidants, such as ascorbic acid, cysteine hydrochloride, sodium bisulfate, sodium metabisulfite, sodium sulfite and the like; (b) oil-soluble antioxidants, such as ascorbyl palmitate, butylated hydroxytoluene (BHT), lecithin, propyl gallate, alpha-tocopherol and the like; and (c) metal chelating agents, such as citric acid, ethylenediamine tetraacetic acid (EDTA), sorbitol, tartaric acid, phosphoric acid and the like. Pharmaceutically acceptable suspending agents that may, optionally, be included in the compositions of the invention include, for example, ethoxylated isostearyl alcohols, polyoxyethylene sorbitol and sorbitan esters, microcrystalline cellulose and mixtures thereof.

Unit Dosage Forms of Compositions

A unit dosage form of the compositions of the invention will typically comprise a soft or hard gel capsule, gelcap, caplet or other oral dosage form containing a combined amount from about 0.25 ml to about 5 ml of one or more edible oils, and an effective amount of one or more vitamins and/or minerals, which are preferably water soluble, as is described herein. The unit dosage may, optionally, also contain one or more antioxidant agents, suspending agents, and/or emulsification agents as practically needed, or as desired, in quantities that are beneficial, which quantities may readily be determined by those of ordinary skill in the art.

A preferred unit dose of a composition of the invention contains a combined amount of about 700 mg of oils, of which 500 mg is preferably omega-3 oil including 350 mg of DHA and 35 mg EPA. Each unit dose of the one or more edible composition also preferably comprises about 12.5 mg of vitamin B6, about 500 µg of vitamin B12 and about 1000 mg of folic acid (vitamin B9), as well as a trace amount of tocopherol (an antioxidant), as is known in the art. Yellow beeswax and/or lecithin are also preferably included in the compositions of the invention, and are preferably added to the one or more edible oils to act as suspending agents so that the vitamins and/or minerals do not settle during their wait in a hopper for encapsulation. In this unit dose, it is preferred to administer two gel capsules (or other unit dosage form) each day (either two gel capsules together once per day or spaced apart in any desire time interval, such as 1, 2, 3, 4, 5, 6, 7 or 8 hours during the day.

Method of Production

The compositions of the invention may be produced by admixing or otherwise combining the above-described ingredients to form a suspension, or other desired form, of the one or more vitamins and/or minerals in the one or more edible oils using, for example, methods and equipment known by those of skill in the art, followed by an injection or other insertion of the resulting mixture (suspension, emulsion or the like) into hollow oral dosage forms, such as empty gelatin capsules, gelcaps or caplets.

Because, in some cases, some or all of the one or more vitamins and/or minerals may settle out from a suspension, emulsion or other form after a short period of time, the composition is preferably mixed one or more times, using known or other mixing, circulating, stirring or shaking techniques, prior to inserting the composition into the hollow gelatin capsules or other oral dosage forms. Such mixing, which should permit the composition to be uniformly inserted into two or more of the hollow oral dosage forms, is preferably performed immediately prior to such insertion. However, the mixing can be performed at any time prior to such insertion that is effective for permitting the composition to be uniformly inserted into two or more of the hollow oral dosage forms. This period of time, and the number of times that the composition should be mixed, may vary depending upon a wide variety of circumstances, such as the number of oral dosage forms being filled and the number and quantities of water-soluble or other vitamins and/or minerals and edible oils that are present in the composition, or whether suspending agents are utilized and may readily be determined by those of skill in the art. Once the composition is inserted into or encapsulated within, the hollow oral dosage form, it generally is no longer necessary to have the one or more water-soluble or other vitamins and/or minerals suspended, or otherwise distributed, within the one or more edible oils. A mammal that consumes one or more filled gelatin capsules (or other oral dosage forms) should receive approximately the same amount of water-soluble or other vitamins and/or minerals and edible oils once the capsules, gelcaps, caplets or other oral dosage forms dissolve, disintegrate or otherwise decompose, whether the composition is present in the form of a suspension, an emulsion or some other form, or in the form of water-soluble vitamins and/or minerals that have settled out from a suspension.

The following example describes and illustrates one of the compositions of the present invention, and methods for preparing such compositions. This example is intended to be merely illustrative of the present invention, and not limiting thereof in either scope or spirit. Those of skill in the art will readily understand that variations of certain of the conditions and/or steps employed in the procedures described in the example can be used to prepare these compositions.

A mixture containing edible oils, fish oil and sunflower oil and solid-state particles of vitamin B6, B9 and B12, with each of the three B vitamins present in the form of a finely divided uniformly mixed powder is prepared as follows. Sunflower oil is mixed with yellow beeswax and heated to 145° F. causing the beeswax to melt. The mixture of sunflower oil and melted beeswax is then transferred to a larger vessel, where it is blended with lecithin. The beeswax and lecithin are present in quantities sufficient to enhance the ability of the solid-state vitamins to remain at least temporarily in suspension. This mixture is then blended into fish oil, including amounts of DHA and EPA such that the final mixture includes DHA in an amount which is about 50 weight percent of the total weight of edible oils and EPA in an amount which is about 5 weight percent of the total weight of the edible oils. The mixture is allowed to come to approximately 80° F. Thereafter, the solid-state particles of the vitamins are added to the blend of the edible oils and the beeswax and lecithin. This mixture is thoroughly blended, at approximately 70° F., so as to assure content uniformity, and added to a hopper of a conventional soft-gel capsule, gelcap, or caplet manufacturing device. Soft-gel ribbons are combined around unit doses of the mixture to produce a semi-finished capsule, gelcap, or caplet. Optionally ascorbyl palmitate may be added at the time the vitamin particles are added. It is also anticipated that the vitamins may or may not be coated at the time they are added to the mixture. The vitamins may, for example, be coated with an edible oil, such as vegetable oil, prior to mixing. Furthermore, tocopherols or vitamin E may optionally be added to the fish oil and vitamin B12 may be triturated with anhydrous ascorbic acid used as a diluent for the vitamin mixture.

To minimize oxidation of the fish oil and other edible oils that may be used in the invention, nitrogen may be used. For example, nitrogen may be used to displace atmospheric oxygen in the head space within a container holding the oil. Also, a "nitrogen blanket" may be used as is known to those of skill in the art to further minimize oxidation of the oil during the mixing stages and where it is otherwise being handled. Alternatively, the mixing could take place within a vacuum to minimize oxidation of the oil.

In its raw form, gelatin is a thick, syrupy liquid. By the process of cooling and manipulating, it is turned into a ribbon and laid out on a sheet. This sheet is fed around the outer surfaces of two dyes and rolled together. Two dyes in the shape of a soft gel rotate and come together. As they come together, the fill material from the hopper is injected. Heat and pressure form the capsule, gelcap, or caplet into a hermetically sealed mold. The soft gels are very delicate when they come off the machine. A conventional drying process hardens them into the finished product.

Prior to packaging, the gel capsules, gelcaps, or caplets (or other unit dosage form), may, optionally, be irradiated in order to kill microorganisms that may have become be present therein or thereon during production or otherwise. Such irradiation should be performed at a level, and for a period of time, that does not diminish or destroy the effectiveness of any of the edible oils or vitamins and/or minerals contained therein.

The resulting gelatin capsules, gelcaps, caplets or other unit dosage forms may then be packaged in any manner known by those of skill in the art for packaging vitamins, minerals, oils pharmaceutical products or similar items.

Gel caps may be produced using known methods from a variety of different types of gelatin, for example, type A gelatin, type B gelatin or gelatin that is Kosher. Different types of gelatin can be obtained from commercial sources that are known by those of skill in the art, such as Post Apple Scientific (North East, Pa.), or be produced using known methods.

Gelatin is a protein that can be extracted using standard extraction techniques from a product that results after a partial hydrolysis of collagenous raw material, which may be obtained from the skin, white connective tissue, or bones of animals. For example, collagen, the precursor of gelatin, can be pretreated for about 10-30 hours with a 1-5% mineral acid for type A gelatin production or for about 35-90 days in a liming process with a lime slurry for type B gelatin production. Type A gelatin exhibits the isoionic point at pH 7.0-9.5, whereas type B gelatin, due to domination in the liming process, exhibits the isoionic point at 4.8-5.2. Type A gelatin can be manufactured from frozen or fresh edible-grade pig skins or from bone ossein. Most of type B gelatin comes from bones. While most edible gelatin is of type A, but type B gelatin is also used. Pieces of bone generally are pretreated with either mineral acid (for type A gelatin) or lime (for type B gelatin) in the manner described above, and then demineralized in 4-7% hydrochloric acid for a period of about 7-14 days. The demineralized bone pieces then undergo a standard liming procedure and the resulting materials are washed, and subsequently subjected to about four or five extractions, which generally take from about 4 to 8 hours each, at increased temperatures, which generally range from about 131-212° F. The resulting extracts, which generally contain from about 3-7% gelatin, are then filtered, concentrated in a vacuum, evaporated, chilled, extruded as noodles, and dried at a temperature generally ranging from about 86-140° F. The resulting dry gelatin can then be ground and blended to required or desired specifications.

SPECIFIC PREFERRED EMBODIMENTS

Other preferred embodiments of the compositions of the invention comprise specific combinations of two or more ingredients. These embodiments of the invention include, for example, the following combinations: (a) one fatty acid or other edible oil with one vitamin and/or mineral; (b) one fatty acid or other edible oil with more than one vitamin and/or mineral; (c) two or more fatty acids or other edible oils with one vitamin and/or mineral; (d) two or more fatty acids or other edible oils with two or more vitamins and/or minerals; or (e) any of (a)-(d) optionally in combination with one or more other ingredients that are suitable for use in an oral pharmaceutical or other oral dosage compositions, and that do not prevent, or substantially reduce, the effectiveness of the compositions. Any one or more of the vitamins may be in a solid state, a solubilized state, or some other state, and various compositions of the invention may include both solid state and/or solubilized vitamins. In addition, The quantities of the one or more fatty acids and/or other edible oils and vitamins and/or minerals that may be employed in these compositions need not be the same. For example, the compositions may contain a larger quantity of EPA than DHA (or other fatty acids), a larger quantity of DHA than EPA (or other fatty acids), etc. As another example, the compositions may contain a larger quantity of one of the B vitamins, such as B6, B9 or B12, than another B or other vitamin; or more vitamin B6 than either vitamin B9 or B12; or any combination thereof.

As further examples, compositions within the invention may include one edible oil and vitamins B6, B9 and B12 (one edible oil and three different B vitamins) more than one edible oil and any one vitamin B; more than one edible oil and vitamins B6, B9, and B12 (more than one edible oil and three different B vitamins); or any combination thereof.

As still further examples, compositions within the invention may include one or more edible oils, for example fish oil and/or sunflower oil, with vitamin C alone or in combination with B6, B9, and/or B12 admixed therein, and with one or more oil soluble vitamins, for example vitamin A, dissolved in the fish oil or other edible oil. Other oil soluble vitamins may be dissolved in the edible oil, including but not limited to vitamins D, E, and K.

The compositions of the invention may also be in the form of an emulsion, such as a water-in-oil emulsion, an oil-in-water-in-oil emulsion, or the like, with at least one of the phases of the emulsion including the one or more vitamins and/or minerals suspended (if solid-state particles) or dissolved therein. For example, an "water-in-oil" emulsion is a mixture of two or more immiscible liquids that are generally held in suspension by one or more emulsifiers, and in which one or more oils constitutes the "continuous phase" and water or an aqueous solution is the "disperse phase."

The compositions of the invention, in the form of emulsions, may be prepared using any edible emulsifier (any edible substance that aids in the formation and/or maintenance of an emulsion), such as egg yolk or egg lecithin, and standard emulsification techniques and equipment known by those of skill in the art. For example, water-in-oil emulsions may generally be formed by hand or mechanical stirring or whisking of the continuous and disperse phases of the emulsions for a period of time, and at a strength, that permits the aqueous phase to break down into droplets, which are preferably small in size.

Other emulsions may be formed by slowly adding one or more ingredients employed in the compositions of the invention to one or more other ingredients while simultaneously mixing the ingredients rapidly. This disperses and suspends tiny droplets of one liquid throughout another liquid. The two liquids would generally rapidly separate if an emulsifier were not added to the mixture. Emulsifiers generally function as liaisons between two liquids and serve to stabilize the resulting mixture. Eggs and gelatin are among the foods that contain emulsifiers. Chemically, emulsions are colloids, heterogeneous mixtures composed of tiny particles suspended in another immiscible (unmixable) material. These particles are larger than molecules, but less than about one one-thousandth of a millimeter (0.001 mm). Particles having such a size generally do not settle out of an emulsion and can pass through filter paper. The particles in a colloid can be solid, liquid or bubbles of gas. The medium that they are suspended in can be a solid, liquid or gas (although gas colloids cannot be suspended in gas). Emulsions are liquid-liquid colloids, tiny liquid droplets suspended in another liquid. Emulsions are usually thick in texture and satiny in appearance. Microemulsions, which are special kinds of stabilized emulsions in which the dispersed droplets are extremely small (<100 nm), and which are thermodynamically stable, may also be used. A solid emulsion, which is a colloidal dispersion of a liquid in a solid, such as opal or pearl, may also be used.

Additional information concerning emulsification techniques, equipment and ingredients that may be employed to prepare compositions of the invention is present in S. Friberg et al., Food Emulsions (Marcel Dekker, $3^{rd}$ Rev. Ex Ed., 1997), and in V. Vaclavik et al., Essentials of Food Science (Kluwer Academic/Plenum Publishers, $2^{nd}$ Ed., 2003).

Packaging

The compositions of the invention are preferably packaged in a partially or totally opaque container. The package may include a label that indicates how to administer the compositions, for example, the daily dosage, the dosing regimen, whether to take the composition with food or on an empty stomach, whether to avoid taking the composition with alcoholic beverages, etc.

All of the edible oils, other materials and equipment employed in the example, and generally employed to make and use the compositions of the present invention, and to carry out the methods of the present invention, are commercially available from sources known by those of skill in the art, isuch as Cargill, Incorporated (Minneapolis, Minn.), BASF Corp. (Mt. Olive, N.J.), RFI Ingredients (Blauvelt, N.Y.), Hoffmann-LaRoche Inc. (Nutley, N.J.), Martek Corp. (Columbia, Md.), Ocean Nutrition Canada, Ltd. (Bedford, Nova Scotia, Canada), Pronova Biocare AS (Lysakar, Norway), Napro AS (Brattvaag, Norway), DSM (Heerlen, NL), Berg Lipotech AS (Norway), ADM Food Oils (Decatur, Ill.), Oilseeds International, Ltd. (San Francisco, Calif.), and Post Apple Scientific (North East, Pa.).

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow, and that such claims be interpreted as broadly as is reasonable.

Throughout this document, various books, patents, journal articles, web sites, federal regulations and other publications have been cited. The entireties of each of these books, patents, journal articles, web sites, federal regulations and other publications are hereby incorporated by reference herein.

What is claimed is:

1. A composition for an oral administration to a mammal comprising:
   (a) one or more water soluble vitamins or minerals, or combination thereof, in a combined amount that is effective for providing or enhancing a nutritional, medical or other health benefit to the mammal, wherein the one or more water soluble vitamins or minerals are in a form that is capable of being mixed with one or more edible oils;
   (b) one or more edible oils in a combined amount that is effective for permitting the one or more water soluble vitamins or minerals to be mixed therewith, said one or more edible oils containing DHA in an amount greater than about 50 weight percent of the total weight of the edible oils; and,
   wherein said DHA is present in a triglyceride form and the one or more water soluble vitamins or minerals are admixed with the one or more edible oils, and wherein said composition is in a unit dosage form.

2. The composition of claim 1 further comprising one or more antioxidant agents in a combined amount that is effective for preventing or reducing an oxidation, degradation or decomposition of the one or more water soluble vitamins or minerals or the one or more edible oils, wherein the one or more antioxidant agents are admixed with the one or more water soluble vitamins or minerals and the one or more edible oils.

3. The composition of claim 1 where the water soluble vitamins or minerals are coated with one or more edible oils and have an enhanced ability to travel through the stomach to the intestinal tract of the mammal without being degraded.

4. The composition of claim 1 further comprising oil soluble vitamins or minerals.

5. The composition of claim 1, wherein the one or more edible oils includes one or more additional fatty acids.

6. The composition of claim 5, wherein at least one of the one or more additional fatty acids is one or more omega-3 fatty acid.

7. The composition of claim 6, wherein the one or more additional omega-3 fatty acid is EPA or ALA, or combinations thereof.

8. The composition of claim 1, wherein the composition includes one or more vitamins, and wherein at least one of the one or more vitamins is a B-vitamin.

9. The composition of claim 8, wherein the one or more B-vitamins is vitamin B6, vitamin B9 or vitamin B12, or combination thereof.

10. The composition of claim 1 wherein the water soluble vitamins or minerals are in a form that is capable of being at least temporarily suspended within the one or more edible oils.

11. A composition for an oral administration by a mammal comprising:
   (a) one or more solid-state particles of one or more water soluble vitamins or minerals in a combined amount that is effective for providing or enhancing a nutritional, medical or other health benefit to the mammal;
   (b) one or more edible oils containing DHA in an amount greater than about 50 weight percent of the total weight of the edible oils and optionally containing one or more additional fatty acids, wherein the one or more additional fatty acids are omega-3 fatty acids, omega-6 fatty acids or omega-9 fatty acids, and wherein the one or more additional fatty acids are in a combined amount that is effective for permitting the solid state particles to be at least temporarily suspended therein;

wherein said DHA is present in a triglyceride form and the solid state particles are admixed with the one or more edible oils or at least temporarily suspended therein and wherein said composition is in a unit dosage form.

12. The composition of claim 11, wherein the oral dosage form is a gelatin capsule.

13. The composition of claim 11 further comprising one or more antioxidant agents in an amount that is effective for preventing or reducing an oxidation, degradation or decomposition of the one or more water soluble vitamins or minerals or the one or more edible oils, wherein the one or more antioxidant agents are admixed with the one or more water soluble vitamins or minerals and the one or more edible oils.

14. The composition of claim 11 where the water soluble vitamins or minerals are coated with one or more edible oils and have an enhanced ability to travel through the stomach to the intestinal tract of the mammal without being degraded.

15. The composition of claim 11 further comprising oil soluble vitamins or minerals.

16. A composition for an oral administration to a mammal comprising:
  (a) one or more solid-state particles of one or more water soluble vitamins, wherein the one or more water soluble vitamins are vitamin B6, vitamin B9 or vitamin B12, or a combination thereof, and wherein the one or more water soluble vitamins are in a combined amount that is effective for providing or enhancing a nutritional, medical or other health benefit to the mammal;
  (b) one or more edible oils containing DHA in an amount greater than about 50 weight percent of the total weight of the edible oils and optionally including one or more additional omega-3 fatty acids in a combined amount that is effective for providing or enhancing a nutritional, medical or other health benefit to the mammal; and
  wherein said DHA is present in a triglyceride form and the solid-state particles are mixed with the one or more edible oils or at least temporarily suspended therein, and wherein said composition is in a unit dosage form.

17. The composition of claim 16, wherein the oral dosage form is a gelatin capsule.

18. The composition of claim 16 wherein the one or more additional omega-3 fatty acids is EPA or ALA, or a combination thereof.

19. The composition of claim 18 wherein the composition includes Vitamin B9, and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid or polyglutamyl derivatives of tetrahydrofolate.

20. The composition of claim 16 wherein the composition includes vitamin B12, and wherein the vitamin B12 is in the form of cyanocobalamin, cobalamin or cobalamin bound to recombinant intrinsic factor.

21. A composition for an oral administration to a mammal comprising:
  (a) one or more solid-state particles of one or more water soluble vitamins, wherein the one or more water soluble vitamins are vitamin B6, vitamin B9 or vitamin B12, or a combination thereof, and wherein the one or more water soluble vitamins are in a combined amount that is effective for providing or enhancing a nutritional, medical or other health benefit to the mammal;
  (b) one or more edible oils containing DHA in an amount greater than about 50 weight percent of the total weight of the edible oils and optionally including one or more additional omega-3 fatty acids in a combined amount that is effective for providing or enhancing a nutritional, medical or other health benefit to the mammal; and
  wherein said DHA is present in a triglyceride form and the solid-state particles are mixed with the one or more edible oils or at least temporarily suspended therein, said vitamin B12 is triturated with anhydrous ascorbic acid, and wherein said composition is in a unit dosage form.

22. The composition of claim 16 wherein the vitamins are coated with an edible oil prior to mixing with the one or more edible oils including one or more omega-3 fatty acids.

23. The composition of claim 16 wherein an amount of one or more suspending agents in a combined amount that is sufficient to provide or enhance an ability of the solid-state particles to remain, at least temporarily, in suspension is blended with one or more edible oils or combination thereof.

24. The composition of claim 23 wherein the suspending agents are beeswax or lecithin, or a combination thereof.

25. The composition of claim 16 where the water soluble vitamins or minerals have an enhanced ability to travel through the stomach to the intestinal tract of the mammal without being degraded.

26. A composition for an oral administration to a mammal comprising:
  (a) one or more solid-state particles of one or more water soluble vitamins, wherein the one or more water soluble vitamins are vitamin B6, vitamin B9 or vitamin B12, or a combination thereof, and wherein the one or more water soluble vitamins are in a combined amount that is effective for providing or enhancing a nutritional, medical or other health benefit to the mammal;
  (b) one or more edible oils containing DHA in an amount greater than about 50 weight percent of the total weight of the edible oils and optionally including one or more additional omega-3 fatty acids in a combined amount that is effective for providing or enhancing a nutritional, medical or other health benefit to the mammal; and
  (c) an oil soluble vitamins or minerals or combination thereof,
wherein said DHA is present in a triglyceride form and the solid-state particles are mixed with the one or more edible oils or at least temporarily suspended therein, and wherein said composition is in a unit dosage form.

27. The composition of claim 16 wherein vitamin B6 is included in an amount ranging from about 1 mg to about 50 mg, vitamin B9 is included in an amount ranging from about 100 mg to about 1000 mg, and vitamin B 12 is included in an amount ranging from about 200 mg to about 2000 mg.

28. A composition for an oral administration to a mammal comprising:
  (a) one or more water soluble vitamins or minerals, or combination thereof, in a combined amount that is effective for providing or enhancing a nutritional, medical or other health benefit to the mammal, wherein the one or more water soluble vitamins or minerals are combined with an amount of water that is sufficient to form an aqueous solution;

(b) one or more edible emulsifiers in a combined amount that is effective to cause or enhance the formation of an emulsion;

(c) one or more edible oils in a combined amount that is effective for forming an oil phase of an emulsion, the one or more edible oils containing DHA in an amount greater than about 50 weight percent of the total weight of the edible oils;

wherein said DHA is present in a triglyceride form and the aqueous solution is combined with the one or more emulsifiers and the one or more edible oils in a manner that forms an emulsion and wherein said composition is in a unit dosage form.

29. The composition of claim 28 wherein the oral dosage form is a gelatin capsule.

30. A method for preparing a composition for an oral administration to a mammal comprising:

(a) providing one or more solid state particles of one or more water soluble vitamins or minerals, or combination thereof;

(b) providing one or more edible oils including one or more fatty acids in a combined amount that is effective for permitting the one or more water soluble vitamins or minerals to be at least temporarily suspended therein said one or more edible oils contains DHA in a triglyercide form in an amount greater than about 50 weight percent of the total weight of the edible oils;

(c) optionally, mixing the one or more water soluble vitamins or minerals, or combination thereof, for a period of time and under conditions that are sufficient to produce a uniform mixture of the one or more water soluble vitamins or minerals, or combination thereof;

(d) optionally, mixing the one or more edible oils for a period of time and under conditions that are sufficient to produce a uniform mixture of the one or more edible oils;

(e) suspending, at least temporarily, an amount of the one or more water soluble vitamins or minerals, or combination thereof, within an amount of the one or more edible oils, or combination thereof, that is effective for producing a suspension of the solid-state particles of the one or more water soluble vitamins or minerals, or combination thereof, within the one or more edible oils, or mixtures thereof;

(f) injecting a resulting suspension into an oral dosage form, wherein the oral dosage faun is hard or soft capsule, gelatin capsule, caplet or gelatin caplet.

31. The method of claim 30 wherein the one or more water-soluble vitamins are vitamin B6, vitamin B9 or vitamin B 12, or combination thereof.

32. The method of claim 31 wherein vitamin B9 is provided and wherein the vitamin B9 is in the form of L-5-methyltetrahydrofolate, (6S)-tetrahydrofolic acid, 5 methyl-(6S)-tetrahydrofolic acid, 5 formyl-(6S)-tetrahydrofolic acid, 10 formyl-(6R)-tetrahydrofolic acid, 5,10-methylene-(6R)-tetrahydrofolic acid, 5,10-methenyl-(6R)-tetrahydrofolic acid, 5-formimino-(6S)-tetrahydrofolic acid, (6S)-5-methyltetrahydrofolic acid or polyglutamyl derivatives of tetrahydrofolate.

33. The method of claim 31 wherein vitamin B12 is provided and wherein the vitamin B12 is in the form of cyanocobalamin, cobalamin or cobalamin bound to recombinant intrinsic factor.

34. The method of claim 31 wherein vitamin B12 is provided and wherein the vitamin B12 is triturated with anhydrous ascorbic acid.

35. The method of claim 30 wherein an amount of one or more suspending agents in a combined amount that is sufficient to provide or enhance an ability of solid-state particles to remain, at least temporarily, in suspension is provided and wherein the one or more suspending agents is blended with the one or more edible oils or combination thereof.

36. The method of claim 30 wherein the one or more fatty acids are omega-3 fatty acids, omega-6 fatty acids or omega-9 fatty acids, or combination thereof.

37. The method of claim 36 wherein the one or more fatty acids are one or more omega-3 fatty acids or combination thereof.

38. The method of claim 37 wherein the composition includes one or more omega-3 fatty acids and wherein the one or more omega-3 fatty acids are DHA, EPA or ALA, or combination thereof.

39. A method for preparing a composition for an oral administration to a mammal comprising:

(a) providing one or more solid-state particles of one or more water soluble vitamins or minerals or combination thereof;

(b) mixing the solid-state particles in an amount of water that is sufficient to form an aqueous solution;

(c) providing one or more edible emulsifiers or a combination thereof;

(d) providing one or more edible oils or combination thereof, said one or more edible oils contains DHA in a triglyceride form in an amount greater than about 50 weight percent of the total weight of the edible oils; including one or more fatty acids;

(e) optionally, mixing the one or more edible oils or combination thereof for a period of time and under conditions that are sufficient to produce a uniform mixture of the one or more edible oils;

(f) mixing the aqueous solution with the one or more edible emulsifiers or combination thereof and the one or more edible oils or combination thereof under conditions that are sufficient to form an emulsion;

(g) injecting the emulsion into a hollow oral dosage form that is a soft or hard capsule, gelatin capsule, caplet or gelatin caplet.

40. A method for enhancing the nutrition, health or medical condition of a mammal comprising:

(a) providing an effective amount of a composition according to claim 1;

(b) orally administering the effective amount of the composition according to claim 1 to a mammal.

41. A method for enhancing the nutrition, health or medical condition of a mammal comprising:

(a) providing an effective amount of a composition according to claim 16;

(b) orally administering the effective amount of the composition according to claim 16 to a mammal.

42. A composition for an oral administration to a mammal comprising:

(a) one or more solid-state particles of one or more water soluble vitamins, wherein the one or more water soluble vitamins are vitamin B6, vitamin B9, or vitamin B12, or a combination thereof, and wherein the one or more water soluble vitamins are in a combined amount that is effective for providing or enhancing a nutritional, medical or other health benefit to the mammal;

(b) one or more edible emulsifiers in a combined amount that is effective to cause or enhance the formation of an emulsion;

(c) one or more edible oils containing one or more additional fatty acids, having DHA in an amount greater than about 50 weight percent of the total weight of the edible oils and the DHA is present in a triglyceride form, wherein the one or more additional fatty acids are omega-3 fatty acids, omega-6 fatty acids or omega-9 fatty acids, and NYC 96717 wherein the one or more additional fatty acids are in a combined amount that is effective for permitting the solid state particles to be at least temporarily suspended therein; and wherein the composition is in a unit dosage form.

43. The composition of claim 42 wherein vitamin B6 is included in an amount ranging from about 1 mg to about 50 mg, vitamin B9 is included in an amount ranging from about 100 mcg to about 1000 mcg, and vitamin B 12 is included in an amount ranging from about 200 mcg to about 2000 mcg.

44. The composition of claim 42, wherein the DHA is present in said composition in an amount of about 350 mg.

* * * * *